(12) United States Patent
Rademacher et al.

(10) Patent No.: US 9,598,479 B2
(45) Date of Patent: Mar. 21, 2017

(54) NANOPARTICLE-PEPTIDE COMPOSITIONS

(75) Inventors: Thomas Rademacher, Oxfordshire (GB); Phillip Williams, Oxfordshire (GB)

(73) Assignee: Midatech Ltd., Abingdon, Oxfordshire (GB)

( * ) Notice: Subject to any disclaimer, the term of this patent is extended or adjusted under 35 U.S.C. 154(b) by 149 days.

(21) Appl. No.: 14/343,083

(22) PCT Filed: Sep. 7, 2012

(86) PCT No.: PCT/EP2012/067561
§ 371 (c)(1),
(2), (4) Date: Apr. 1, 2014

(87) PCT Pub. No.: WO2013/034126
PCT Pub. Date: Mar. 14, 2013

(65) Prior Publication Data
US 2014/0341938 A1 Nov. 20, 2014

Related U.S. Application Data

(60) Provisional application No. 61/531,745, filed on Sep. 7, 2011.

(51) Int. Cl.
*A61K 47/48* (2006.01)
*C07K 14/47* (2006.01)
*C07K 7/06* (2006.01)
*C07K 7/08* (2006.01)
*C07K 14/77* (2006.01)
*A61K 38/38* (2006.01)
*A61K 39/00* (2006.01)

(52) U.S. Cl.
CPC .... *C07K 14/4748* (2013.01); *A61K 47/48861* (2013.01); *A61K 47/48884* (2013.01); *C07K 7/06* (2013.01); *C07K 7/08* (2013.01); *C07K 14/77* (2013.01); *A61K 38/38* (2013.01); *A61K 39/0011* (2013.01); *A61K 2039/55516* (2013.01); *A61K 2039/572* (2013.01); *A61K 2039/60* (2013.01); *A61K 2039/627* (2013.01)

(58) Field of Classification Search
CPC ................................. A61K 47/48; A61K 9/141
See application file for complete search history.

(56) References Cited

U.S. PATENT DOCUMENTS

| | | | |
|---|---|---|---|
| 2005/0100928 A1* | 5/2005 | Hedley | A61K 39/0011 435/6.14 |
| 2006/0246095 A1* | 11/2006 | Peretz et al. | 424/277.1 |
| 2009/0104268 A1* | 4/2009 | Himmler et al. | 424/489 |
| 2009/0297614 A1* | 12/2009 | Rademacher et al. | 424/490 |

FOREIGN PATENT DOCUMENTS

| | | | | |
|---|---|---|---|---|
| GB | WO 2007122388 A2 * | 11/2007 | ............ | A61K 33/24 |
| WO | 2006/037979 A2 | 4/2006 | | |
| WO | 2007/015105 A2 | 2/2007 | | |
| WO | 2010/023247 A1 | 3/2010 | | |
| WO | 2010/042876 A1 | 4/2010 | | |
| WO | 2011/025572 A1 | 3/2011 | | |
| WO | 2011/089921 A1 | 7/2011 | | |
| WO | 20131034741 A1 | 3/2013 | | |

OTHER PUBLICATIONS

Yang et al., "The Protective Immune Response against Infectious Bronchitis Virus Induced by Multi-Epitope Based Peptide Vaccines", Biosci. Biotechnol. Biochem, 2009, pp. 1500-1504.*
Wiesmüller et al.,"Solid phase peptide synthesis of lipopeptide vaccines eliciting epitope-specific B-, T-helper and T-killer cell response",1992, Int. J. Peptide Protein Res., pp. 255-260.*
Wang et al., "CTL epitopes for influenza A including the H5N1 bird flu; genome-, pathogen- and HLA-wide screening", Vaccine, 2007; pp. 2823-2831.*
Velders, Markwin P. et al., "Defined Flanking Spacers and Enhanced Proteolysis Is Essential for Eradication of Established Tumors by an Epitope String DNA Vaccine", Journal of Immunology, 166(1): 5366-5673 (2001).
International Search Report and Written Opinion issued Nov. 20, 2012 in corresponding International Application No. PCT/EP2012/067561.
Ojeda, Rafael et al., "Preparation of multifunctional glyconanoparticles as a platform for potential carbohydrate-based anticancer vaccines", Carbohydrate Research, 342: 448-459 (2007).

(Continued)

*Primary Examiner* — Lianko Garyu
(74) *Attorney, Agent, or Firm* — Patrick J. Hagan; Dann, Dorfman, Herrell and Skillman

(57) ABSTRACT

The present invention provides nanoparticles and compositions comprising such nanoparticles, as well as methods for intracellular delivery of peptides, and methods of producing nanoparticles and related products. The nanoparticles comprise a core comprising a metal and/or a semiconductor atom; and a corona comprising a plurality of ligands covalently linked to the core, wherein at least a first ligand of said plurality comprises a carbohydrate moiety that is covalently linked to the core via a first linker, and wherein at least a second ligand of said plurality comprises a peptide of choice that is covalently linked to the core via a second linker. The second linker comprises a peptide portion and a non-peptide portion, wherein said peptide portion of said second linker comprises the sequence $X_1 X_2 Z_1$, wherein: $X_1$ is an amino acid selected from A and G; $X_2$ is an amino acid selected from A and G; and $Z_1$ is an amino acid selected from Y and F.

18 Claims, 25 Drawing Sheets

(20 of 25 Drawing Sheet(s) Filed in Color)

(56) References Cited

OTHER PUBLICATIONS

Daftarian, Pirouz M. et al., "Rejection of large HPV-16 expressing tumors in aged mice by a single immunization of VacciMax encapsulated CTL/T helper peptides", Journal of Translational Medicine, 5: 26 (2007).

Directive and Notice of Reasons for Rejection, dated Sep. 10, 2015, issued in corresponding Japanese Patent Application No. 2014-529001.

U.S. Official Action, dated Oct. 23, 2015, issued in related U.S. Appl. No. 14/343,435, filed May 14, 2014.

* cited by examiner

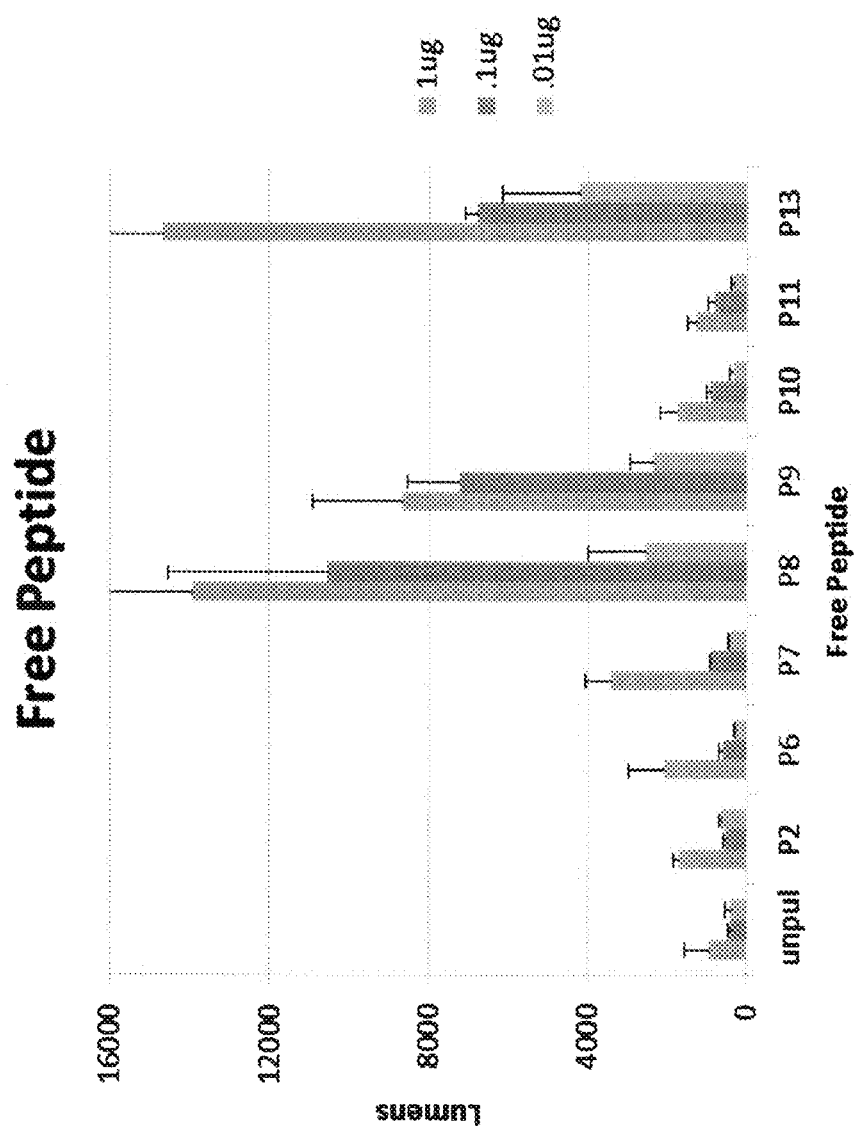

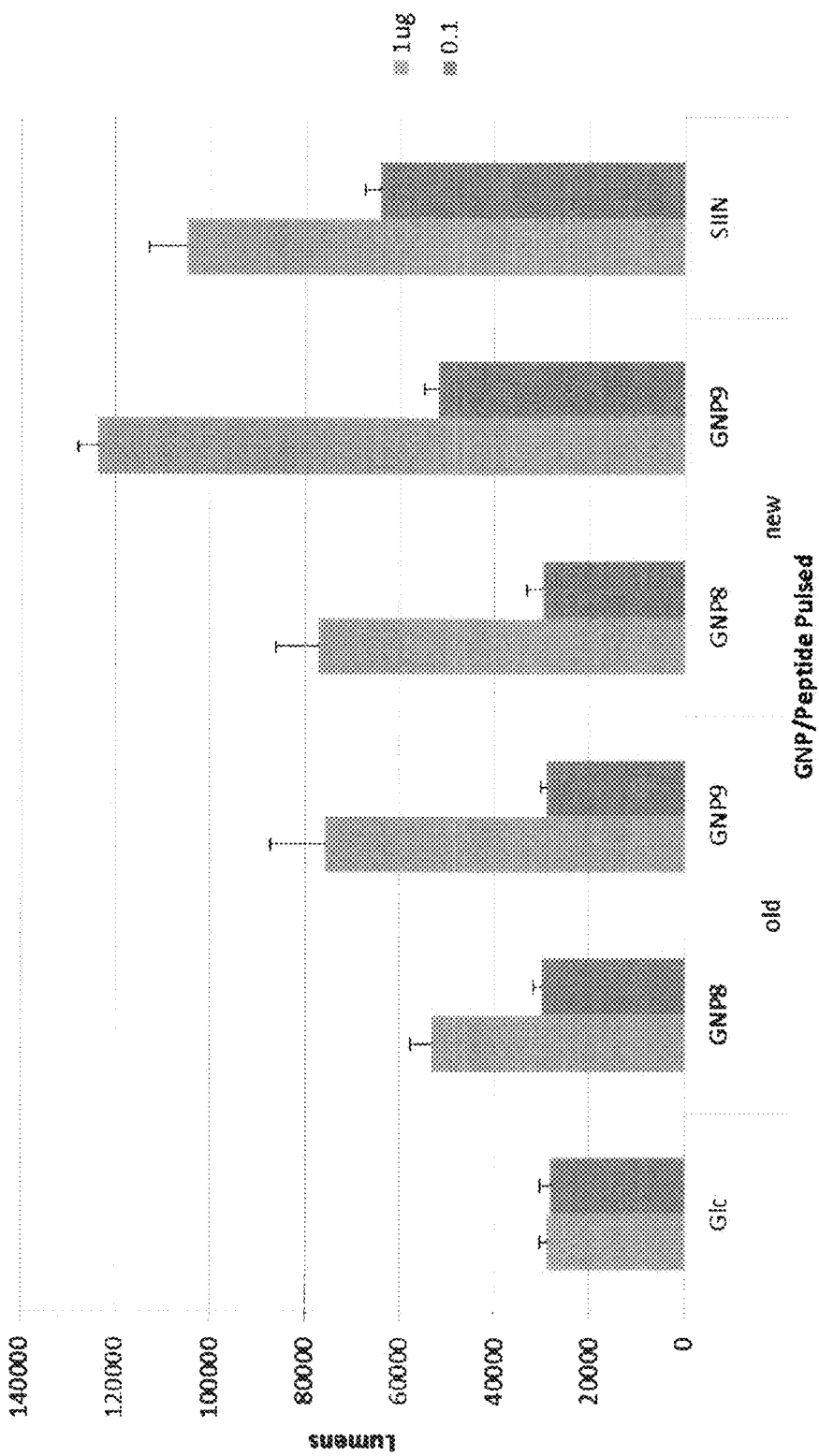

NANOPARTICLE-PEPTIDE COMPOSITIONS

CROSS-REFERENCE TO RELATED APPLICATIONS

This application is the U.S. National Stage of International Application No. PCT/EP2012/067561, filed Sep. 7, 2012, which claims benefit of U.S. Provisional Patent Application No. 61/531,745, filed Sep. 7, 2011. The entire disclosure of each of the aforesaid applications is incorporated by reference in the present application.

FIELD OF THE INVENTION

The present invention relates to substances and compositions useful in intracellular peptide delivery, in particular nanoparticle-mediated delivery of peptides. In certain cases, the invention relates to intracellular delivery of epitopic peptides, e.g., to induce a T cell response. Intracellular peptide delivery may be employed for therapeutic and/or prophylactic treatment of, in particular, tumours and/or pathogen-mediated disease, such as bacterial, viral or parasite infection.

BACKGROUND TO THE INVENTION

A significant challenge for the design and development of peptide-based therapy, such as immunotherapy, is the intracellular delivery of the peptides to intracellular compartments. An example of this is the need to deliver antigen peptides to the antigen processing machinery such that the peptides are presented bound to a class I MHC molecule and thereby stimulate a CTL response. Other examples include delivery of peptide-based drugs to intracellular drug targets. In particular, free peptides often display poor uptake by cells.

One approach that has been employed to date, is to deliver peptides to a intracellular location by administering a vector, such as a viral vector, containing a polynucleotide that encodes the peptide of choice such the that cell can be transfected with the vector and the peptide is produced by the cellular translational machinery. A further example of a strategy to deliver a peptide to an intracellular location is described in Muders et al., 2009, *Clin Cancer Res*, Vol. 15(12), pp. 4095-4103, in which a GIPC-PDZ-targeting peptide was delivered to certain pancreatic tumour cells. The peptide was modified by N-terminal myristolation.

However, there remains a need for further methods and compositions for intracellular delivery of peptides, e.g., in order to induce an immune response or for the administration of certain peptide-based drugs. The present invention addresses these and other needs.

WO 2006/037979 describes nanoparticles comprising antigens and adjuvants, and immunogenic structures comprising the nanoparticles.

BRIEF DESCRIPTION OF THE INVENTION

Broadly, the present invention relates to nanoparticle-based intracellular delivery of peptides. The present inventors have found that the nanoparticles of the invention, described herein, which have a corona including a peptide of choice that is covalently attached to the core of the nanoparticle via particular linkers, are capable of being taken up by cells and thereby delivering the peptide of choice to an intracellular target. As described herein, the peptide of choice may then be released from the nanoparticle, e.g. by specific cleavage processes, so as to free the peptide of choice for interaction with an intracellular target. One example of this is the delivery of an epitopic peptide to an APC for processing and presentation via a class I MHC molecule such that a CTL response may be generated.

Accordingly, in a first aspect the present invention provides a nanoparticle comprising:
(i) a core comprising a metal and/or a semiconductor atom;
(ii) a corona comprising a plurality of ligands covalently linked to the core, wherein at least a first ligand of said plurality comprises a carbohydrate moiety that is covalently linked to the core via a first linker or wherein said first ligand of said plurality comprises glutathione, and wherein at least a second ligand of said plurality comprises a peptide of choice that is covalently linked to the core via a second linker, said second linker comprising:
  a peptide portion and a non-peptide portion, wherein said peptide portion of said second linker comprises the sequence $X_1X_2Z_1$, wherein:
    $X_1$ is an amino acid selected from A and G;
    $X_2$ is an amino acid selected from A and G; and
    $Z_1$ is an amino acid selected from Y and F.

In some cases in accordance with the present invention the non-peptide portion of the second linker comprises C2-C15 alkyl and/or C2-C15 glycol, for example a thioethyl group or a thiopropyl group.

In some cases in accordance with the present invention the first ligand and/or said second ligand are covalently linked to the core via a sulphur-containing group, an amino-containing group, a phosphate-containing group or an oxygen-containing group.

In some cases in accordance with the present invention said peptide portion of said second linker comprises or consists of an amino acid sequence selected from:
(i) AAY; and
(ii) FLAAY (SEQ ID NO: 1).

In certain preferred cases, said second linker is selected from the group consisting of:
(i) HS—$(CH_2)_2$—CONH-AAY;
(ii) HS—$(CH_2)_2$—CONH-FLAAY (SEQ ID NO: 1);
(iii) HS—$(CH_2)_3$—CONH-AAY;
(iv) HS—$(CH_2)_3$—CONH-FLAAY (SEQ ID NO: 1);
(v) HS—$(CH_2)_{10}$—$(CH_2OCH_2)_7$—CONH-AAY; and
(vi) HS—$(CH_2)_{10}$—$(CH_2OCH_2)_7$—CONH-FLAAY (SEQ ID NO: 1),
wherein said second linker is covalently linked to said core via the thiol group of the non-peptide portion of the linker.

Preferably, the peptide of choice is linked via its N-terminus to said peptide portion of said second linker.

In some cases in accordance with the present invention said second ligand is selected from the group consisting of:
(i) HS—$(CH_2)_2$—CONH-AAY$Z_2$;
(ii) HS—$(CH_2)_2$—CONH-FLAAY$Z_2$ (SEQ ID NO: 1);
(iii) HS—$(CH_2)_3$—CONH-AAY$Z_2$;
(iv) HS—$(CH_2)_3$—CONH-FLAAY$Z_2$ (SEQ ID NO: 1);
(v) HS—$(CH_2)_{10}$—$(CH_2OCH_2)_7$—CONH-AAY$Z_2$; and
(vi) HS—$(CH_2)_{10}$—$(CH_2OCH_2)_7$—CONH-FLAAY$Z_2$ (SEQ ID NO: 1),
wherein $Z_2$ represents said peptide of choice.

In some cases in accordance with the present invention said peptide of choice is an epitopic peptide that binds to a class I Major Histocompatibility Complex (MHC) molecule or is capable of being processed so as to bind to a class I MHC molecule.

In some cases in accordance with the present invention said peptide of choice consists of a sequence of 8 to 40 amino acid residues. In particular, the peptide of choice may consists of a sequence of 8 to 12 amino acid residues.

In some cases in accordance with the present invention the peptide of choice is an epitopic peptide that is capable of being presented by a class I MHC molecule so as to stimulate a Cytotoxic T Lymphocyte (CTL) response.

In some cases in accordance with the present invention the peptide of choice forms at least a portion of or is derived from a Tumour-Associated Antigen (TAA) or a viral-, bacterial-, or parasite-associated antigen. In particular, the TAA may be a lung cancer antigen. The lung cancer may in some cases be selected from: small-cell lung carcinoma and any non-small-cell lung carcinoma, optionally wherein said non-small-cell lung carcinoma comprises an adenocarcinoma. The pathogen-associated antigen may in some cases be a viral, bacterial or parasite antigen.

In some cases in accordance with the present invention, the carbohydrate moiety of said first ligand comprises a monosaccharide and/or a disaccharide. In particular, said carbohydrate moiety may comprise glucose, mannose, fucose and/or N-acetylglucosamine.

In some cases in accordance with the present invention, said plurality of ligands comprises one or more ligands selected from the group consisting of: glucose, N-acetylglucosamine and glutathione, in addition to the one or more ligands comprising said peptide of choice.

In some cases in accordance with the present invention, said plurality of ligands comprises:
(a) glucose;
(b) N-acetylglucosamine;
(c) glutathione;
(d) glucose and N-acetylglucosamine;
(e) glucose and glutathione;
(f) N-acetylglucosamine and glutathione; or
(g) glucose, N-acetylglucosamine and glutathione,
in addition to said ligand comprising said peptide of choice.

In some cases in accordance with the present invention said first linker comprises C2-C15 alkyl and/or C2-C15 glycol.

In some cases in accordance with the present invention said first ligand comprises 2'-thioethyl-β-D-glucopyranoside or 2'-thioethyl-α-D-glucopyranoside covalently attached to the core via the thiol sulphur atom.

In some cases in accordance with the present invention, the nanoparticle comprises at least 10, at least 20, at least 30, at least 40 or at least 50 carbohydrate-containing ligands and/or glutathione ligands.

In some cases in accordance with the present invention the nanoparticle comprises at least 1, at least 2, at least 3, at least 4 or at least 5 peptide-containing ligands.

In some cases in accordance with the present invention, the molar ratio of carbohydrate-containing ligands and/or glutathione ligands to peptide-containing ligands is in the range 5:1 to 100:1, such as in the range 10:1 to 30:1.

In some cases in accordance with the present invention the diameter of the core of the nanoparticle is in the range 1 nm to 5 nm.

In some cases in accordance with the present invention the diameter of the nanoparticle including its ligands is in the range 5 nm to 20 nm, optionally 5 nm to 15 nm or 8 nm to 10 nm.

In some cases in accordance with the present invention the core comprises a metal selected from the group consisting of: Au, Ag, Cu, Pt, Pd, Fe, Co, Gd and Zn, or any combination thereof.

In some cases in accordance with the present invention the core is magnetic.

In some cases in accordance with the present invention the core comprises a semiconductor. In particular, the semiconductor may in some cases be selected from the group consisting of: cadmium selenide, cadmium sulphide, cadmium tellurium and zinc sulphide.

In some cases in accordance with the present invention the core is capable of acting as a quantum dot.

In some cases in accordance with the present invention the nanoparticle comprises at least two peptide of choice-containing ligands, and wherein the peptide of choice of each of the at least two peptide of choice-containing ligands differ.

In some cases in accordance with the present invention the peptides of choice of said at least two peptide of choice-containing ligands each form at least a portion of or are each derived from one or more antigens, such as TAAs. In some cases in accordance with the present invention the peptides of choice of said at least two peptide of choice-containing ligands each form at least a portion of or are each derived from a different lung cancer TAA.

In a further aspect, the present invention provides a composition comprising a plurality of nanoparticles in accordance with the first aspect of the invention. The composition may further comprise at least one pharmaceutically acceptable carrier, salt and/or diluent.

In some cases in accordance with the present invention the composition comprises a first species of nanoparticle having a first peptide of choice-containing ligand and a second species of nanoparticle having a second peptide of choice-containing ligand, wherein the peptides of choice of said first and second species differ. The peptides of choice of each of said first and second species of nanoparticle may in some cases form at least a portion of or each be derived from one or more antigens, such as TAAs.

In some cases in accordance with the present invention the composition of the invention may comprise a pool of at least 3, at least 4, at least 5 or at least 10 different species of nanoparticle, each species having a different peptide of choice.

The composition may further comprise at least one adjuvant, which adjuvant may optionally be covalently attached to the core of at least one nanoparticle. Alternatively, the composition of the invention may be substantially free of adjuvant or the only adjuvant effect may be provided by the nanoparticles.

In a further aspect the present invention provides a vaccine comprising a composition of the invention. The vaccine may be for therapeutic or prophylactic treatment of a cancer, including lung cancer.

In a further aspect the present invention provides a nanoparticle, composition or vaccine of the invention, for use in medicine.

The nanoparticle, composition or vaccine may be for use in a method of treatment of a cancer or a pathogen infection in a mammalian subject.

In a further aspect, the present invention provides use of a nanoparticle, composition or vaccine of the invention in the preparation of a medicament for the treatment of a cancer or a pathogen infection in a mammalian subject.

The nanoparticle, composition or vaccine of the invention may be for administration via lymphatic uptake.

In a further aspect, the present invention provides a method of prophylactic or therapeutic treatment of a cancer or a pathogen infection, comprising administering a prophylactically or therapeutically sufficient amount of a nanoparticle, composition or vaccine to a mammalian subject in need thereof. In some cases in accordance with said method aspect of the present invention, said nanoparticle, composition or vaccine is administered via a route selected from the group consisting of:
- injection into an organ or tissue of a mammalian subject at, or in the vicinity of, a site of lymphatic uptake;
- nasal delivery via a spray or gel;
- buccal delivery via a spray or gel or orally dissolvable film;
- oral delivery via a dissolvable film;
- transdermal delivery via a patch incorporating the nanoparticle; and
- inhalation delivery of a composition comprising the nanoparticle.

In a further aspect, the present invention provides an in vitro or in vivo method for generating a Cytotoxic T Lymphocyte (CTL) response, comprising:
(i) contacting at least one antigen presenting cell (APC) with at least one nanoparticle of the invention, such that said peptide of choice is presented on a class I MHC molecule of said APC; and
(ii) contacting said at least one APC of (i) with at least one CTL cell, such that said CTL cell is activated by said APC to generate a CTL response that is specific for said peptide of choice, wherein said peptide of choice is an epitopic peptide.

In some cases in accordance with the present invention the APC is cultured in the presence of said nanoparticle, and, simultaneously or sequentially, co-cultured with said CTL cell. Optionally, the APC may be subjected to a washing step after being contacted with the nanoparticle before being co-cultured with said CTL cell. In some cases, the method may further comprise administering the CTL cell to a mammalian subject.

In some cases in accordance with the present invention the nanoparticle may be delivered by a route of administration selected from the group consisting of:
- injection into an organ or tissue of a mammalian subject at, or in the vicinity of, a site of lymphatic uptake;
- nasal delivery via a spray or gel;
- buccal delivery via a spray or gel or orally dissolvable film;
- oral delivery via a dissolvable film
- transdermal delivery via a patch incorporating the nanoparticle; and
- inhalation delivery of a composition comprising the nanoparticle.

In some cases, said at least one nanoparticle comprises a pool of nanoparticles having different peptides of choice.

In a further aspect, the present invention provides a method of producing a nanoparticle according of the invention, comprising:
- derivatising the carbohydrate with the first linker;
- derivatising the peptide of choice with the second linker; and
- reacting the first linker-derivatised carbohydrate and the second linker-derivatised peptide of choice with reactants for producing the core of the nanoparticle so that during self-assembly of the nanoparticle, the nanoparticle core attaches the carbohydrate and the peptide of choice via their respective linkers. In some cases, the reaction mixture comprises the derivatised carbohydrate, the derivatised peptide of choice, a salt of the metal and/or semiconductor atoms and a reducing agent to produce the nanoparticle. Additionally or alternatively, said carbohydrate may be replaced by, or supplemented by, glutathione.

In certain cases in accordance with this and other aspects of the invention the reaction product, including the nanoparticle, is subjected to a purification step to remove unreacted free peptide, optionally wherein the purification step comprises running the reaction product through a G-50 Sephadex™ column.

In certain cases in accordance with this and other aspects of the invention the method may further comprise the step of formulating the nanoparticle into a composition with at least one pharmaceutically acceptable carrier, salt or diluent.

In certain cases in accordance with this and other aspects of the invention the method is for attaching said peptide of choice via said second linker to said nanoparticle such that the nanoparticle with the peptide of choice attached is capable of being internalised by a cell.

In certain cases in accordance with this and other aspects of the invention the method is for attaching said peptide of choice via said second linker to said nanoparticle such that the nanoparticle with the peptide of choice attached is capable of being internalised by an antigen presenting cell (APC).

In a further aspect, the present invention provides a method for intracellular delivery of a peptide of choice, comprising contacting a cell with a nanoparticle or composition of the invention.

In a further aspect, the present invention provides a use of a nanoparticle or composition of the invention for the intracellular delivery of the peptide of choice.

The present invention includes the combination of the aspects and preferred features described except where such a combination is clearly impermissible or is stated to be expressly avoided. These and further aspects and embodiments of the invention are described in further detail below and with reference to the accompanying examples and figures.

BRIEF DESCRIPTION OF THE FIGURES

The application file contains at least one drawing executed in color. Copies of this application with color drawings will be provided by the Patent and Trademark Office upon request and payment of the necessary fee.

DETAILED DESCRIPTION OF THE INVENTION

Figure 1A:
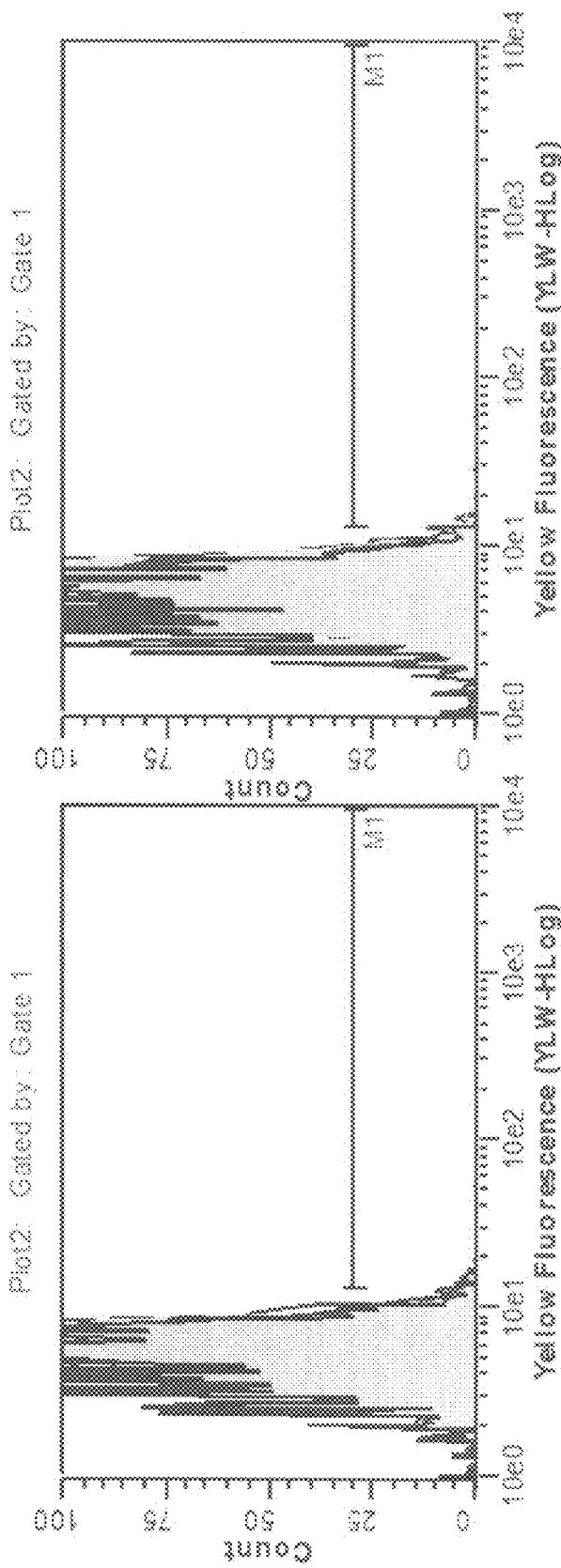
FIG. 1 shows SIINFEKL (SEQ ID NO: 2) presentation from GNP: LKb cells were seeded into 24-well plates and allowed to adhere overnight. Next, GNPs were pulsed to the equivalent of 1 ug/mL peptide (Green), 0.1 ug/mL (Blue), or 0.01 ug/mL (Red). After two hours, cells were washed, and subjected to (A-D) flow cytometric labelling with 25.D1.16 (Angel) antibody, or (E) combined with B3Z CTL for overnight co-culture. The next day, cells were lysed and Beta-galactosidase activity was measured.
Figure 1B:
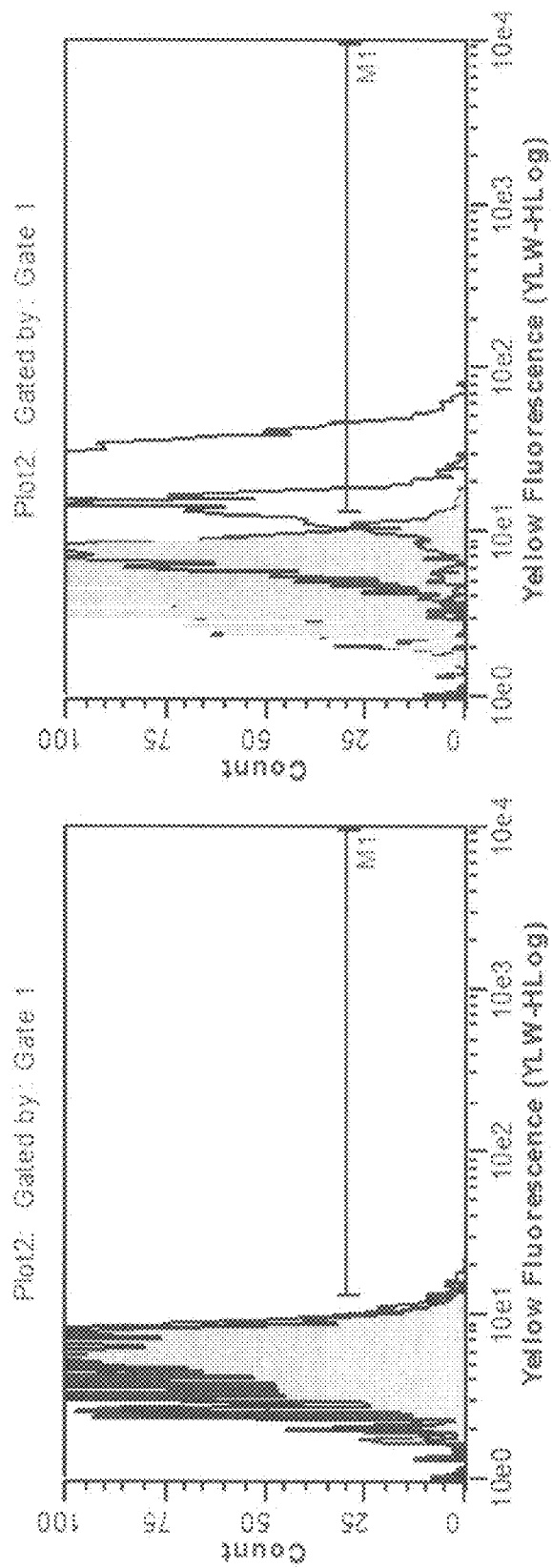
Figure 1C:
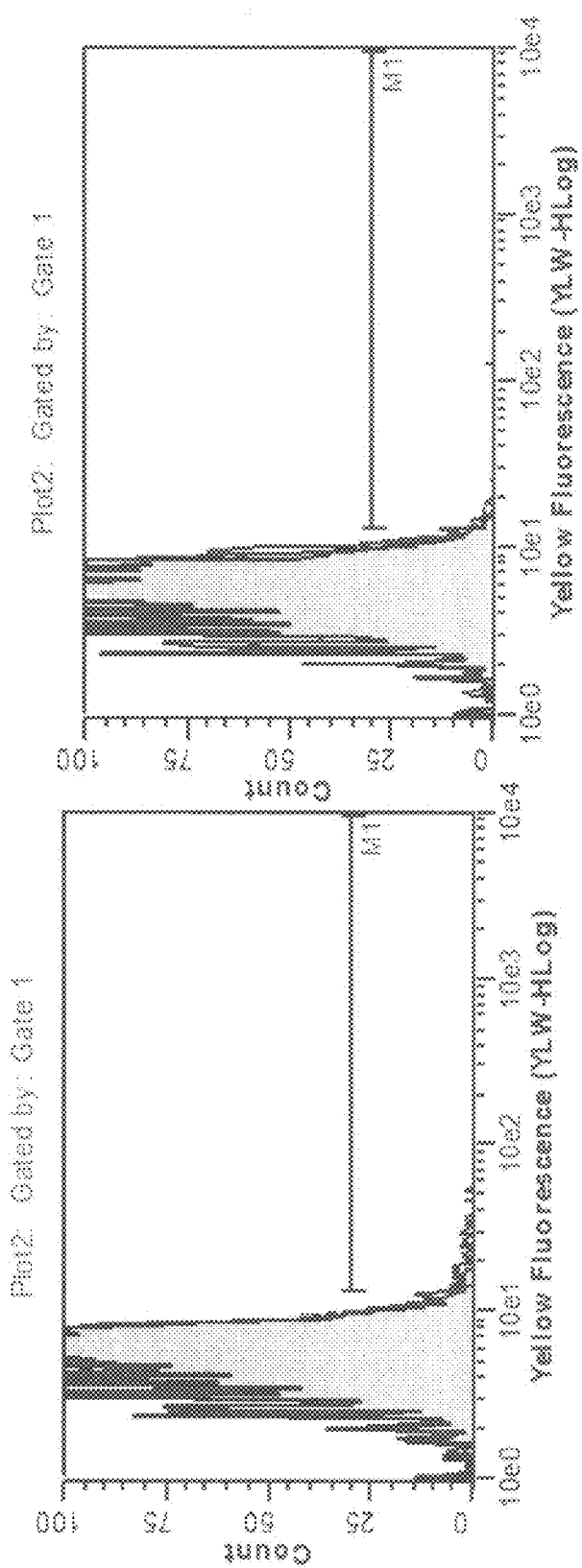
Figure 1D:
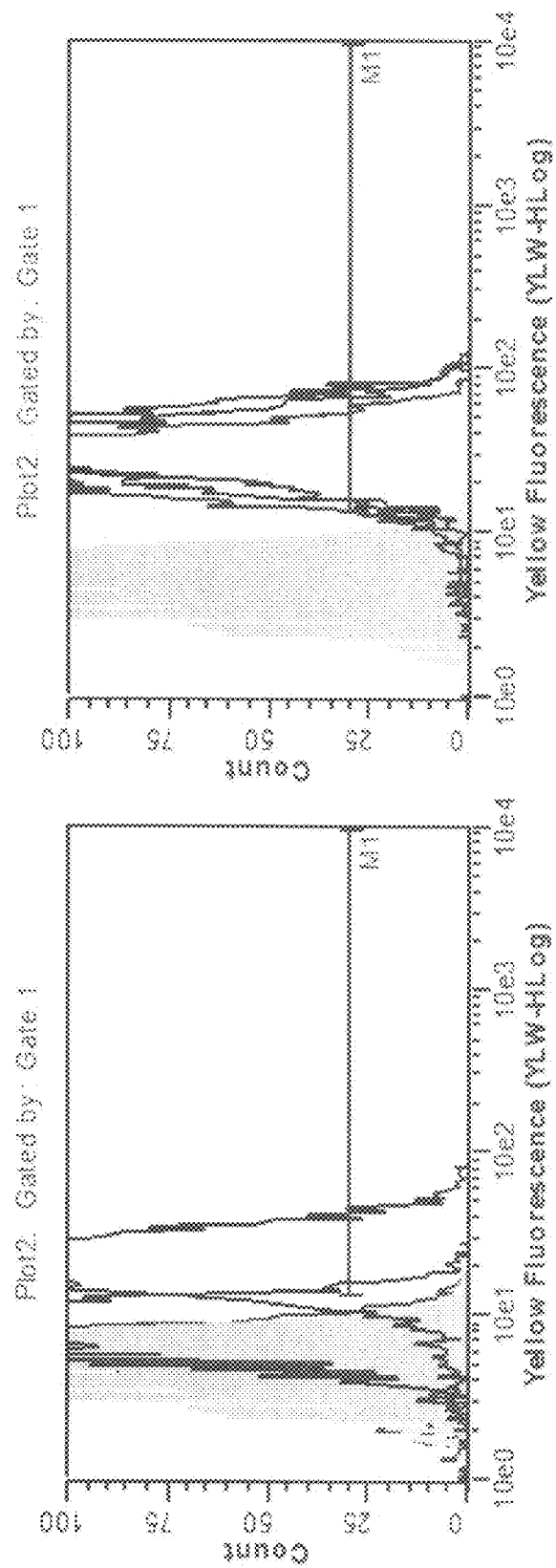

In describing the present invention, the following terms will be employed, and are intended to be defined as indicated below.

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticles may find use in accordance with the present invention. Moreover, gold-coated nanoparticles comprising a magnetic core of iron oxide ferrites (having the formula $XFe_2O_4$, where X=Fe, Mn or Co) functionalised with organic compounds (e.g. via a thiol-gold bond) are described in EP2305310 (the entire contents of which is expressly incorporated herein by reference) and are specifically contemplated for use as nanoparticles/nanoparticle cores in accordance with the present invention.

As used herein, "corona" refers to a layer or coating, which may partially or completely cover the exposed surface of the nanoparticle core. The corona includes a plurality of ligands which include at least one carbohydrate moiety, one surfactant moiety and/or one glutathione moiety. Thus, the corona may be considered to be an organic layer that surrounds or partially surrounds the metallic core. In certain embodiments the corona provides and/or participates in passivating the core of the nanoparticle. Thus, in certain cases the corona may include a sufficiently complete coating layer substantially to stabilise the metal-containing core. However, it is specifically contemplated herein that certain nanoparticles having cores, e.g., that include a metal oxide-containing inner core coated with a noble metal may include a corona that only partially coats the core surface. In certain cases the corona facilitates solubility, such as water solubility, of the nanoparticles of the present invention.

Nanoparticles

Nanoparticles are small particles, e.g. clusters of metal or semiconductor atoms, that can be used as a substrate for immobilising ligands.

Preferably, the nanoparticles have cores having mean diameters between 0.5 and 50 nm, more preferably between 0.5 and 10 nm, more preferably between 0.5 and 5 nm, more preferably between 0.5 and 3 nm and still more preferably between 0.5 and 2.5 nm. When the ligands are considered in addition to the cores, preferably the overall mean diameter of the particles is between 5.0 and 100 nm, more preferably between 5 and 50 nm and most preferably between 5 and 10 nm. The mean diameter can be measured using techniques well known in the art such as transmission electron microscopy.

The core material can be a metal or semiconductor and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometer range. Other particularly useful core materials are doped with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or the quantum dots described elsewhere in this application.

Nanoparticle cores comprising semiconductor atoms can be detected as nanometer scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the core of the nanoparticles may be magnetic and comprise magnetic metal atoms, optionally in combination with passive metal atoms. By way of example, the passive metal may be gold, platinum, silver or copper, and the magnetic metal may be iron or gadolinium. In preferred embodiments, the passive metal is gold and the magnetic metal is iron. In this case, conveniently the ratio of passive metal atoms to magnetic metal atoms in the core is between about 5:0.1 and about 2:5. More preferably, the ratio is between about 5:0.1 and about 5:1. As used herein, the term "passive metals" refers to metals which do not show magnetic properties and are chemically stable to oxidation. The passive metals may be diamagnetic or superparamagnetic. Preferably, such nanoparticles are superparamagnetic.

Examples of nanoparticles which have cores comprising a paramagnetic metal, include those comprising $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$.

Other magnetic nanoparticles may be formed from materials such as MnFe (spinel ferrite) or CoFe (cobalt ferrite) can be formed into nanoparticles (magnetic fluid, with or without the addition of a further core material as defined above. Examples of the self-assembly attachment chemistry for producing such nanoparticles is given in Biotechnol. Prog., 19:1095-100 (2003), J. Am. Chem. Soc. 125:9828-33 (2003), J. Colloid Interface Sci. 255:293-8 (2002).

In some embodiments, the nanoparticle or its ligand comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}$Tc, which exists in a variety of oxidation states although the most stable is $TcO^{4-}$; $^{32}$P or $^{33}$P; $^{57}$Co; $^{59}$Fe; $^{67}$Cu which is often used as $Cu^{2+}$ salts; $^{67}$Ga which is commonly used a $Ga^{3+}$ salt, e.g. gallium citrate; $^{68}$Ge; $^{82}$Sr; $^{99}$Mo; $^{103}$Pd; $^{111}$In which is generally used as $In^{3+}$ salts; $^{125}$I or $^{131}$I which is generally used as sodium iodide; $^{137}$Cs; $^{153}$Gd; $^{153}$Sm; $^{158}$Au; $^{186}$Re; $^{201}$Tl generally used as a $Tl^{+}$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Additionally or alternatively, the nanoparticles of the present invention, or the results of their interactions with other species, can be detected using a number of techniques well known in the art using a label associated with the nanoparticle as indicated above or by employing a property of them. These methods of detecting nanoparticles can range from detecting the aggregation that results when the nanoparticles bind to another species, e.g. by simple visual inspection or by using light scattering (transmittance of a solution containing the nanoparticles), to using sophisticated techniques such as transmission electron microscopy (TEM) or atomic force microscopy (AFM) to visualise the nanoparticles. A further method of detecting metal particles is to employ plasmon resonance that is the excitation of electrons at the surface of a metal, usually caused by optical radiation. The phenomenon of surface plasmon resonance (SPR) exists at the interface of a metal (such as Ag or Au) and a dielectric material such as air or water. As changes in SPR occur as analytes bind to the ligand immobilised on the surface of a nanoparticle changing the refractive index of the interface. A further advantage of SPR is that it can be used to monitor real time interactions. As mentioned above, if the nanoparticles include or are doped with atoms which are NMR active, then this technique can be used to detect the particles, both in vitro or in vivo, using techniques well known in the art. Nanoparticles can also be detected using a system based on quantitative signal amplification using the nanoparticle-promoted reduction of silver (I). Fluorescence spectroscopy can be used if the nanoparticles include ligands as fluorescent probes. Also, isotopic labelling of the carbohydrate can be used to facilitate their detection.

Peptide of Choice

The nanoparticle of the present invention comprises a peptide-containing ligand ("said second ligand") that is covalently linked to the core of the nanoparticle via a linker ("said second linker"). The second ligand comprises a peptide that may be intended for intracellular delivery. This "peptide of choice" may be any suitable peptide. In particular, the peptide may be a fragment of a larger polypeptide that is able to exert an effect when delivered to an intracellular site. In certain cases, the peptide of choice may be a peptide-based drug. In certain cases, the peptide of choice may comprise an epitope (an "epitopic peptide") that gives rise to an immune response when delivered to, for example, an intracellular compartment of an APC. In certain preferred cases, the peptide of choice may be a peptide that binds to a class I Major Histocompatibility Complex (MHC) molecule or is capable of being processed so as to bind to a class I MHC molecule. In some cases in accordance with the present invention, the peptide of choice may consist of a sequence of 8 to 40 amino acid residues, such as a sequence of 8 to 12 amino acid residues. In certain cases, the peptide of choice may be capable of being presented by a class I MHC molecule so as to stimulate a Cytotoxic T Lymphocyte (CTL) response. Such epitopic peptides may form at least a portion of, or be derived from, a Tumour-Associated Antigen (TAA) or a pathogen-associated antigen (e.g. a viral, bacterial or parasite antigen). In some cases, the peptide of choice may be a peptide drug, such as a peptide that targets an intracellular target. One example of such a intracellular targeting peptide is the GIPC-PDZ domain inhibitor described in Muders et al., 2009, *Clin Cancer Res, Vol.* 15(12), pp. 4095-4103 (the entire contents of which is hereby incorporated herein by reference).

Administration and Treatment

The nanoparticles and compositions of the invention may be administered to patients by any number of different routes, including enteral or parenteral routes. Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes.

Administration be performed e.g. by injection, or ballistically using a delivery gun to accelerate their transdermal passage through the outer layer of the epidermis. The nanoparticles can then be taken up, e.g. by dendritic cells, which mature as they migrate through the lymphatic system, resulting in modulation of the immune response and vaccination against the epitopic peptide and/or the antigen from which the epitopic peptide was derived or of which it forms a part. The nanoparticles may also be delivered in aerosols. This is made possible by the small size of the nanoparticles.

The exceptionally small size of the nanoparticles of the present invention is a great advantage for delivery to cells and tissues, as they can be taken up by cells even when linked to targeting or therapeutic molecules. Thus, the nanoparticles may be internalised by cells such as APCs, the peptides processed and released, e.g. for presentation via class I MHC or for interaction with intracellular components.

The nanoparticles of the invention may be formulated as pharmaceutical compositions that may be in the forms of solid or liquid compositions. Such compositions will generally comprise a carrier of some sort, for example a solid carrier such as gelatine or an adjuvant or an inert diluent, or a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicising agent, preservative or anti-oxidant or other materials well known to those skilled in the art. Such materials should be non-toxic and should not interfere with the efficacy of the active ingredient. The precise nature of the carrier or other material may depend on the route of administration, e.g. orally or parenterally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, N.Y., USA); Remington's Pharmaceutical Sciences, 20th Edition, 2000, pub. Lippincott, Williams & Wilkins; and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

Immunotherapy

The compositions of the invention, such as the vaccines as defined in the claims, may in some cases be used for the prophylaxis and treatment of diseases such as cancer, and more particularly for immunotherapy.

In the present invention, the term "vaccination" means an active immunization, that is an induction of a specific immune response due to administration, e.g. via the subcutaneous, intradermal, intramuscular, oral or nasal routes, of small amounts of an antigen which is recognized by the vaccinated individual as foreign and is therefore immunogenic in a suitable formulation. The antigen is thus used as a "trigger" for the immune system in order to build up a specific immune response against the antigen.

In accordance with the present invention, vaccination may be therapeutic or prophylactic. By way of example, it might be possible to achieve a prophylactic protection against the breakout of a cancer disease by vaccination of individuals who do not suffer from cancer. Examples of individuals for whom such a prophylactic vaccination might be applied are individuals who have an increased risk of developing a cancer disease, although this application is not limited to such individuals. Patients being at risk of cancer can already have developed tumours, either as primary tumours or metastases, or show predisposition for cancer.

For the active immunization of cancer patients according to the invention, the nanoparticles are typically formulated as vaccines. Preferably, such pharmaceutical preparations contain a pharmaceutically acceptable carrier which, by way of example, may further comprise auxiliary substances, buffers, salts and/or preserving agents. The pharmaceutical preparations may, e.g., be used for the prophylaxis and therapy of cancer-associated conditions, such as metastasis formation, in cancer patients. In doing so, antigen-presenting cells are specifically modulated in vivo or also ex vivo so as to generate the immune response against the TAAs.

For the active immunization with the specific antigens or the antigen combination usually a vaccine formulation is used which contains the immunogen—be it a natural TAA or its epitope, mimic or neoepitope mimic,—mostly at low concentrations, e.g. in an immunogenic amount ranging from 0.01 µg to 10 mg, yet the dosage range can be increased up a range of 100 to 500 mg. Depending on the immunogenicity of the vaccination antigen which is, e.g., determined by sequences of a foreign species or by derivatization, or also depending on the auxiliary substances or adjuvants, respectively, used, the suitable immunogenic dose can be chosen e.g. in the range of from 0.01 µg to 1 mg, preferably 100 µg to 500 µg. A depot vaccine which is to be delivered to the organism over an extended period of time may, however, also contain much higher amounts of vaccination antigen, e.g. at least 1 mg to more than 100 mg.

The concentration will depend on the amount of liquid or suspended vaccine administered. A vaccine usually is provided in ready-to-use syringes or ampoules having a volume ranging from 0.01 to 1 ml, preferably 0.1 to 0.75 ml.

The vaccination antigen of a component of vaccine preferably is presented in a pharmaceutically acceptable carrier which is suitable for subcutaneous, intramuscular and also intradermal or transdermal administration. A further mode of administration functions via the mucosal pathway, e.g. vaccination by nasal or peroral administration. If solid substances are employed as auxiliary agent for the vaccine formulation, e.g. an adsorbate, or a suspended mixture, respectively, of the vaccine antigen with the auxiliary agent will be administered. In special embodiments, the vaccine is presented as a solution or a liquid vaccine in an aqueous solvent.

Preferably, vaccination units of a tumour vaccine are already provided in a suitable ready-to-use syringe or ampoule. A stable formulation of the vaccine may advantageously be put on the market in a ready to use form. Although a content of preserving agents, such as thimerosal or other preserving agents with an improved tolerability, is not necessarily required, yet it may be provided in the formulation for a longer stability at storage temperatures of from refrigerating temperatures up to room temperature. The vaccine according to the invention may, however, also be provided in frozen or lyophilized form and may be thawed or reconstituted, respectively, upon demand.

In certain cases in accordance with the present invention the immunogenicity of the vaccine of the invention may be increased by by employing adjuvants. For this purpose, solid substances or liquid vaccine adjuvants are used, e.g. aluminum hydroxide (Alu-Gel) or aluminum phosphate, growth factors, lymphokines, cytokines, such as IL-2, IL-12, GM-CSF, gamma interferon, or complement factors, such as C3d, further liposome preparations, or also formulations with additional antigens against which the immune system has already generated a strong immune response, such as tetanus toxoid, bacterial toxins, such as Pseudomonas exotoxins, and derivatives of lipid A and lipopolysaccharide.

In certain cases, no additional adjuvant is employed, in particular, the examples described herein show that efficient generation of a CTL response is achieved using nanoparticles of the invention without any added adjuvant (c.f. free peptides which are generally administered with one or more adjuvants). This is highly beneficial in certain circumstances as a number of adjuvants are considered to be toxic or otherwise unsuitable for human use.

The following is presented by way of example and is not to be construed as a limitation to the scope of the claims.

EXAMPLES

Example 1

Synthesis and Characterisation of Nanoparticles

Test ligands and their identification numbers are given below (Molecular wt);

```
                                                   (SEQ ID NO: 2)
SIINFEKL (963)

(SEQ ID NO: 2)
SIINFEKL-N-(CH2)2-SH (1021)

(SEQ ID NO: 3)
FLSIINFEKL-N-(CH2)2-SH (1280)

(SEQ ID NO: 4)
FLAAYSIINFEKL-N-(CH2)2-SH (1587)

(SEQ ID NO: 5)
AAYSIINFEKL-N-(CH2)2-SH (1325)

(SEQ ID NO: 2)
HS(CH2)2-CONH-SIINFEKL (1051)

(SEQ ID NO: 3)
HS(CH2)2-CONH-FLSIINFEKL (1309)

(SEQ ID NO: 4)
HS(CH2)2-CONH-FLAAYSIINFEKL (1616)

(SEQ ID NO: 5)
HS(CH2)2-CONH-AAYSIINFEKL (1356)

(SEQ ID NO: 2)
HS-(CH2)10-(CH2OCH2)7-CONH-SIINFEKL (1471)

(SEQ ID NO: 3)
HS-(CH2)10-(CH2OCH2)7-CONH-FLSIINFEKL (1732)

(SEQ ID NO: 4)
HS-(CH2)10-(CH2OCH2)7-CONH-FLAAYSIINFEKL (2034)

(SEQ ID NO: 5)
HS-(CH2)10-(CH2OCH2)7-CONH-AAYSIINFEKL (1774)
```

Test NPs were synthesized using 10 μmole Gold Chloride (Aldrich 484385), 30 μmole glucose with a thio ethyl linker (GlcC2) and 1.5 μmole of peptide ligand (variable 1.5-3 mg).

The following method was used; 1.5 μmole peptide was dissolved in 2 ml methanol, followed by the addition of 30 μmole GlcC2 in 200 μl methanol, and 116 μl of aqueous gold chloride containing 10 μmole Au. The sample was vortexed for 30 sec, shaken for approximately 5 min and then under rapid vortexing for a total of 30 sec 200 μl of 1M NaBH₄ was added, tubes were sealed and then gently shaken for 1.5 h.

Samples were bench spun the supernatant removed and the dark pellet dissolved in 2 ml water, and then transferred to a 10 kDa vivaspin for a total of 4 times 2 ml water washes each of 8 min at 5 Krpm.

Nanoparticles (NPs) were removed from the vivaspins and made up to 500 μl with water, they were then subjected to 15 Krpm bench spin to remove any large aggregates.

Gold content post spin/production by in house assay is shown below 100% yield would be 1.97 mg;

| NP | Total mg Au |
|----|-------------|
| 2  | 1.14        |
| 3  | 0.03        |
| 4  | 0.00        |
| 5  | 0.05        |
| 6  | 1.34        |
| 7  | 1.06        |
| 9  | 1.59        |
| 10 | 1.69        |
| 11 | 1.37        |
| 13 | 1.49        |
| Glc| 1.02        |

NPs 3, 4 and 5 showed large near complete aggregation, addition of DMSO to these aggregates failed to solubilise these particle.

The remaining NP samples were respun to remove any further aggregates, and aliquots taken to allow for later analyses, specifically gold and peptide content. One aliquot was made up to 500 μl with water, dated and labelled, these were subsequently used for HLA presentation testing.

The final analysis of these 500 μl samples for HLA presentation was as follows;

| NP | Total μmole Au | nmole peptide* | nmole peptide** |
|----|----------------|----------------|-----------------|
| 2  | 1.46           | 166            | 106             |
| 3  | —              | —              | —               |
| 4  | —              | —              | —               |
| 5  | —              | —              | —               |
| 6  | 3.09           | 348            | 263             |
| 7  | 3.36           | 287            | 219             |
| 9  | 4.77           | 508            | 286             |
| 10 | 4.42           | 256            | 372             |

-continued

| NP | Total µmole Au | nmole peptide* | nmole peptide** |
|---|---|---|---|
| 11 | 3.26 | 235 | 830 |
| 13 | 4.19 | 386 | 1083 |
| Glc | 3.11 | nd | nd |

*BSA Std
**Peptide Std

Ligand ratios used were such that 2 peptides should theoretically be attached to each NP of approximately 100 Au atoms, the data above suggests approximately 6-8 peptides/100 Au atoms. This could simple be an artefact of BCA method (and BSA standard) used for peptide measurement of NP bound peptides or perhaps the peptide ligands attach.

Analysis of peptide content is both crucial and in this case complex, the BCA method was used. Unfortunately gold NPs exhibit large uv/vis absorbance, so in addition to running the test samples aliquots of NPs were also measured in water and blanked against water to determine their absorbance at 565 nm the wavelength used in the BCA assay, this absorbance amounted to approximately 20% of the test sample BCA assay value and was individually corrected for. This correction however, assumes that a peptide NP subjected to BCA analysis will still maintain the same absorbance seen for the free NP on top of the BCA specific component; this is consistent with the high extinction coefficients seen with just pure gold NPs.

In the table above * refers to quantitation related to a BSA standard initially on a weight basis then converted to moles of peptide, in the ** column the individual peptide ligands were used as standards.

Initial analyses using Sephadex G-50 with PBS elution to try to resolve free form NP bound peptide was performed primarily with NP6, suggest that little/no free ligand is contaminating the NP preparations. Iodine was used to release all NP bound ligands the iodine began to appear in the fractions 16+ for FIG. 1.

Larger fraction sizes and equivalent amounts of NP pre and post iodine treatment were then used, the iodine released peptide elutes with a peak in fraction 10, this material appears smaller than the standard peptide possibly because the latter is oxidized/dimeric. Individual corrections were also applied for non peptidic absorbances from NP6, near equivalent areas under the curve were obtained for NP6 corrected and NP6+iodine.

Production of NP8 and 12

NP8 and 12 were successfully produced by the methods above, quantitations given below represent the 500 µl sample subsequently used, which in turn is (60% of the total preparation);

| NP | µmole Au | nmole peptide* |
|---|---|---|
| 8 | 5.28 | 175 |
| 12 | 3.21 | 65 |

*Determined by Coomassie method

Repeat Production of NPs 2-5

NP's 2-5 were produced by a variation using 75% methanol not 95% in the synthesis stage. NP2 produced a 'normal' NP as previously, NPs 3, 4 and 5 as before formed aggregates, these aggregates where not soluble in water, 10% acetic acid, PBS, DMSO or DMF, however 300 mM NaOH did result in total NP solubilisation.

Additional synthesis was carried out using Sephadex G-50 to remove any free peptide. These NPs were made as above but with the following changes:

The free peptides were not fully soluble in MeOH so in addition to the 2 ml MeOH 100 µl water was added plus for P8 70 µl of 1MNaOH and for P9 only 20 µl NaOH that was required to effect full peptide solubilisation. NaOH is compatible with NP synthesis, the water and alkali reduced the final MeOH % post borohydride reduction to 82 and 83.5% for NP8 and NP9 respectively.

An extra wash step was included after the initial spin down post reduction but pre-vivaspin, this was performed with 2 ml MeOH and 100 µl of 1MNaCl.

Post vivaspin half of each preparation was subjected to a Sephadex G-50 column eluted with PBS, fractions collected and aliquots measured for protein by BCA, tight pools of the main proteinaceous peaks were pooled and then resubjected to vivaspin with water washes to effect solvent change.

Only half of the NP preparation was passed down G-50, the resultant profiles and pools were found to be essentially clear of free peptide. The NP brown colouration could be visually seen up to fraction 12, in a separate run 50 ul of the stock preparation was rerun under the same conditions and the 515 nm absorbance measured (which will detect Au NPs not free peptides) and gives an indication if the NP is trailing off the G-50 column.

The final pooled material had the following specifications;

| | NP8 | NP9 |
|---|---|---|
| Volume ml | 0.5 | 0.5 |
| Peptide by BCA (BSA std) µg/ml | 638 | 490 |
| Theoretical peptide µg/ml | 225 | 118 |
| Au mg/ml | 1.30 | 0.81 |

The theoretical values are determined by assuming 44 ligands/100 Au, random competition between the two ligands at the time of NP formation and the Au yield.

NP Ligand Release with Iodide

An aliquot of NP9 was mixed with a 4-fold volume excess of 1M KI and left at 4° C. for 4 days, in order to result in complete ligand release. After 4 days, the material was centrifuged and the clear supernatant passed down G-50 and fractions collected and assayed by BCA. The amount of NP9 post KI assayed was exactly twice that used for the NP9 alone (a correction of 1.1 was applied for inter-assay absorbance differences), the areas were found to be almost exactly 2:1 suggesting complete ligand removal. The amount of ligand released was quantitated using 2 assays; Coomassie and BCA in conjunction with 2 standards peptide 9 and BSA, and is tabulated below.

| Protein std used | Coomassie µg | BCA µg |
|---|---|---|
| BSA | 377 | 611 |
| P9 | 2210 | 1062 |

The data in the table has been corrected up to the total expected yield for the whole preparation.

In conclusion, peptide-containing NPs have been synthesized. The peptide NPs are essentially devoid of contaminating free peptides by simple use of Sephadex G-50 gel filtration chromatography. Iodide was successfully used to release NP bound peptide, and gave quantitative yield data.

Example 2

Evaluation of Presentation Assays

T cell receptors (TCR) are on the surface of T lymphocytes and recognize peptides in the context of major histocompatibility complex (MHC) (1). Generally, antigen presenting cells (APC) contain machinery to process proteins and load them onto empty MHC. While CD4+ T cells recognize MHC Class II (MHCII), CD8+ T cells respond to MHC Class I (MHCI). Conventionally, MHCII peptides derive from endocytosed components of the extracellular milieu. In contrast, MHCI loads peptides processed from an intracellular source (1, 2).

SIINFEKL (SEQ ID NO: 2), a peptide epitope that is derived from ovalbumin (OVA), is presented in the context of a murine MHCI allele termed H-2K$^b$ (3). If OVA is expressed in a murine cell expressing H-2K$^b$, SIINFEKL is presented conventionally. However, if OVA is supplied exogenously, SIINFEKL can be presented by an alternative process known as MHCI cross-presentation (4, 5). In fact, haplotype-matched mouse immunized with OVA generate an immunodominant response to SIINFEKL (SEQ ID NO: 2).

Therefore, many reagents have been developed to assay the presentation of this peptide in an effort to further the understanding of conventional and alternative MHCI presentation. These reagents can be utilized to experiment with the potential chemical linkages of peptides in nanoparticles. Thus, we can uncover which linkage is most easily processed in a mouse cell line.

Results and Discussion

Flow Cytometry as a Measure of Presentation

In order to analyze epitope linkage to nanoparticles, we first optimized a readout assay for the presentation of the epitope released from the nanoparticle. For this purpose, SIINFEKL (SEQ ID NO: 2) presentation in LK$^b$ cells was evaluated. As mentioned earlier, more than one reagent exists. Of the two methods tested, one is flow cytometry-based, while the other is cell-based. The flow cytometry-based method begins with pulsing LK$^b$ cells with differing amounts of SIINFEKL (SEQ ID NO: 2) peptide. After allowing enough time for peptide binding to surface K$^b$ molecules, cells were washed and incubated with the 25.D1.16 antibody which is specific to the SIINFEKL:K$^b$ (SEQ ID NO: 2) complex. Next, the cells were secondarily labelled and subjected to flow cytometry analysis using unpulsed cells as the background reading. It was found that this method detected surface complexes when the cells were pulsed with as little as 5 ng/mL.

T Cell Activation as a Measure of Antigen Presentation

Another form of epitope-specific antigen presentation is the measurement of T cell activation by the MHCI peptide complex. Here, we used B3Z (OVA peptide specific T cell line), which recognizes SIINFEKL (SEQ ID NO: 2) the context of K$^b$. As a convenient measure, this T cell line contains β-galactosidase cloned with the NFAT promoter. Upon peptide recognition and T cell activation, β-galactosidase is expressed and conversion of a detectable substrate serves as an excellent measure of antigen presentation to T cells.

To evaluate this method, we performed a similar experiment as above. LK$^b$ cells were pulsed with SIINFEKL (SEQ ID NO: 2) peptide, washed, and then co-incubated with B3Z T cell line overnight. The next day, cells were lysed and β-galactosidase was measured using a luminescent substrate. As expected, the resolution of this method was similar to the previous method with the limit of detection at approximately 5 ng/mL.

Therefore, both methods exhibit approximately the same resolution and were selected for use in the evaluation of nanoparticle-peptide constructs.

Materials and Methods

Cell Lines

LK$^b$ cells are mouse fibroblasts and were the primary line used. Specifically, they are L929 cells stably expressing the murine H-2K$^b$ molecule.

Synthetic Peptides

Synthetic SIINFEKL (OVA 257-264) (SEQ ID NO: 2) peptides were purchased from Genscript USA (Piscataway, N.J.). Peptides were resuspended to 5 mg/mL in DMSO and pulsed onto cells at the concentration denoted in the figures.

T Cell Hybridomas

The SIINFEKL:Kb-specific T hybridoma (B3Z) (SEQ ID NO: 2) expresses (β-galactosidase upon recognition of peptide-MHC class I complexes and has been described previously (3, 6). T cell hybridomas were maintained in complete RPMI plus 10% FCS and 0.05 mM 2-ME. Activation was measured using the luminescent substrate Galactolight Plus (Applied Biosystems, Foster City, Calif.) according to the manufacturer's instructions. Light intensity was measured using a TopCount NXT plate reader (Perkin Elmer, Waltham, Mass.).

Flow Cytometry

LK$^b$ cells were treated with varying amounts of SIINFEKL (SEQ ID NO: 2) peptides. After a 2 hr incubation, cells were collected, washed once with PBS, and then incubated for 1 hr with 25.D1.16 culture supernatant (monoclonal antibody specific for SIINFEKL (SEQ ID NO: 2) complexed to H-2K$^b$) (7) on ice. Cells were then washed two times in PBS and incubated for 30 min on ice with FITC-labeled goat anti-mouse IgG secondary antibody (Caltag Laboratories, Burlingham, Calif.). Finally, cells were washed two times with PBS and resuspended in PBS+0.1% BSA for flow cytometry on a Guava EasyCyte Plus Flow Cytometer (Millipore, Billerica, Mass.) and analyzed using the accompanying software.

Antigen Presentation Assays

To assay SIINFEKL (SEQ ID NO: 2) presentation using a flow cytometric or cell-based method, we pulsed LK$^b$ cells in a 15 mL conical at 37° C. for 2 hrs. Following this incubation, cells were washed once with PBS and then subjected to detection using flow cytometry or added to B3Z cells at an effector to target ratio of 1:1.

REFERENCES

1. Vyas, J. M., A. G. Van der Veen, and H. L. Ploegh. 2008. The known unknowns of antigen processing and presentation. *Nature reviews* 8:607-618.
2. Hansen, T. H., and M. Bouvier. 2009. MHC class I antigen presentation: learning from viral evasion strategies. *Nature reviews* 9:503-513.
3. Shastri, N., and F. Gonzalez. 1993. Endogenous generation and presentation of the ovalbumin peptide/K$^b$ complex to T cells. *Journal of Immunology* 150:2724-2736.
4. Amigorena, S., and A. Savina. 2010. Intracellular mechanisms of antigen cross presentation in dendritic cells. *Current opinion in immunology* 22:109-117.

5. Blanchard, N., and N. Shastri. 2010. Cross-presentation of peptides from intracellular pathogens by MHC class 1 molecules. *Annals of the New York Academy of Sciences* 1183:237-250.
6. Tewari, M. K., G. Sinnathamby, D. Rajagopal, and L. C. Eisenlohr. 2005. A cytosolic pathway for MHC class II-restricted antigen processing that is proteasome and TAP dependent. *Nature immunology* 6:287-294.
7. Porgador, A., J. W. Yewdell, Y. Deng, J. R. Bennink, and R. N. Germain. 1997. Localization, quantitation, and in situ detection of specific peptide-MHC class I complexes using a monoclonal antibody. *Immunity* 6:715-726.

Example 3

Nanoparticle-Peptide Presentation Assays

The test ligands listed below were constructed and attached to gold nanoparticles (GNP) by the above-described linker chemistry.

```
                                           (SEQ ID NO: 2)
 1. SIINFEKL

2. SIINFEKL-N-(CH2)2-SH (SEQ ID NO: 3)
 3. FLSIINFEKL-N-(CH2)2-SH (SEQ ID NO: 4)
 4. FLAAYSIINFEKL-N-(CH2)2-SH (SEQ ID NO: 5)
 5. AAYSIINFEKL-N-(CH2)2-SH (SEQ ID NO: 2)
 6. HS(CH2)2-CONH-SIINFEKL (SEQ ID NO: 3)
 7. HS(CH2)2-CONH-FLSIINFEKL (SEQ ID NO: 4)
 8. HS(CH2)2-CONH-FLAAYSIINFEKL (SEQ ID NO: 5)
 9. HS(CH2)2-CONH-AAYSIINFEKL (SEQ ID NO: 2)
10. HS-(CH2)10-(CH2OCH2)7-CONH-SIINFEKL (SEQ ID NO: 3)
11. HS-(CH2)10-(CH2OCH2)7-CONH-FLSIINFEKL (SEQ ID NO: 4)
12. HS-(CH2)10-(CH2OCH2)7-CONH-FLAAYSIINFEKL (SEQ ID NO: 5)
13. HS-(CH2)10-(CH2OCH2)7-CONH-AAYSIINFEKL
```

SIINFEKL (SEQ ID NO: 2), an epitope derived from ovalbumin that is presented in the context of the murine MHCI molecule H-2 Kb, was measured using two methods. One method utilized a TCR-like antibody termed 25.D1.16, also referred to as "Angel", that recognize SIINFEKL (SEQ ID NO: 2)/MHCI complex. In addition, we assessed presentation using the B3Z, SIINFEKL (SEQ ID NO: 2) peptide specific CTL hybridoma, which expresses β-galactosidase under the NFAT (CTL signaling molecule) promoter, which upon activation express beta-gal measured by a light emitting substrate.

A. Analysis of GNP

Figure 1E:
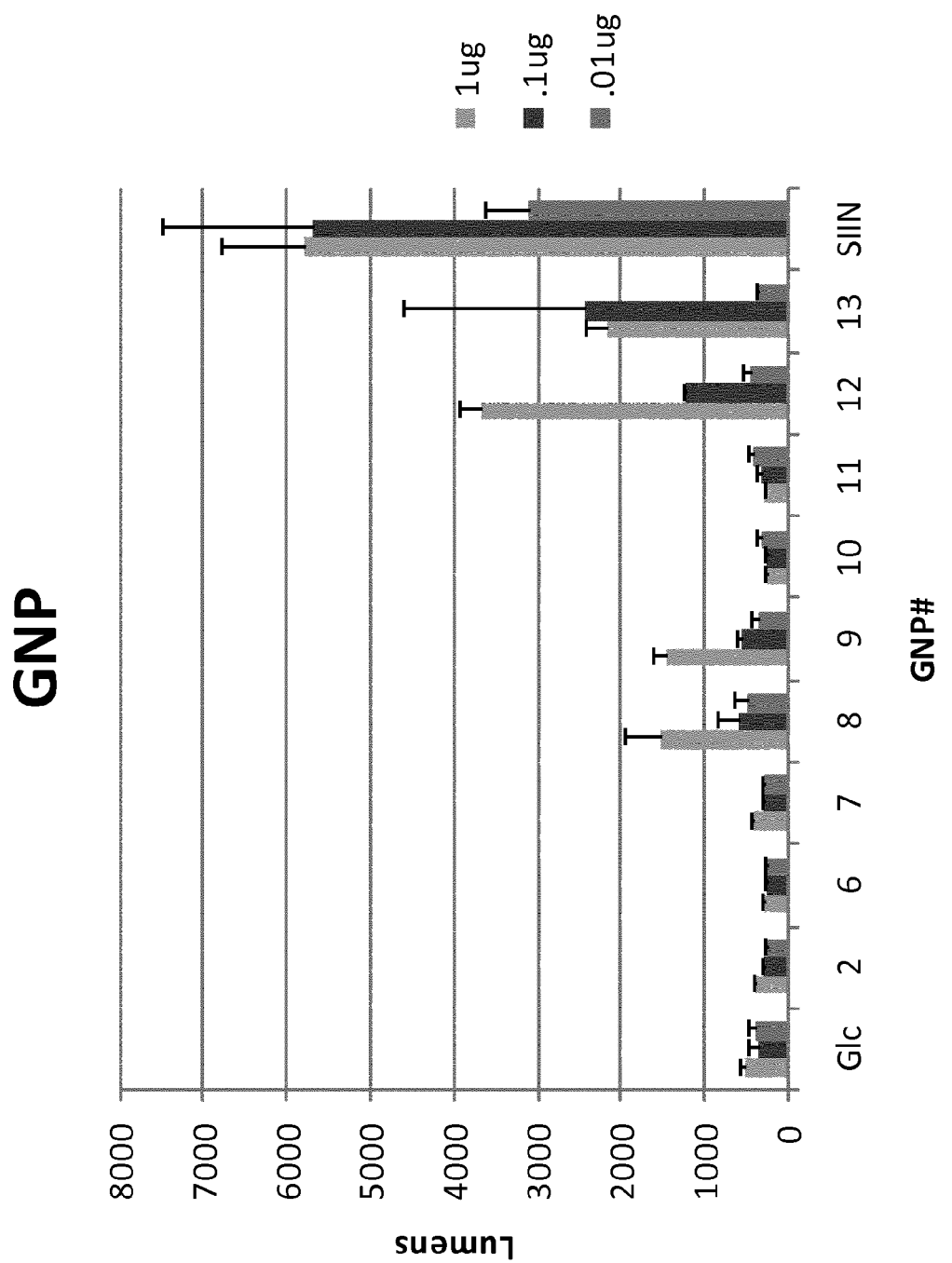

To assess the ability of cells to process and present SIINFEKL associated with GNP, we used L-Kb murine fibroblasts. As demonstrated in FIG. 1, GNPs 8, 9, 12, and 13 displayed good processing and presentation. This was found to be the case for both flow cytometric (FIG. 1A-D—processing) and CTL-based methods (FIG. 1E—presentation). Thus, FLAAYSIINFEKL (SEQ ID NO: 4) and AAYSIINFEKL (SEQ ID NO: 5) exhibited superior in vitro SIINFEKL (SEQ ID NO: 2) processing (the underlined portion showing the peptide portion of the linker. Also, as illustrated in FIG. 1E, HS—(CH2)10-(CH2OCH2)7-CONH chemistry was found to be better processed than HS(CH2)2-CONH. However, HS(CH2)2-CONH was still found to be processed very efficiently. Additionally, we note a dose-dependent reduction of presentation with no detection at 0.01 µg/mL.

B. Analysis of Free Peptide

Figure 2A:
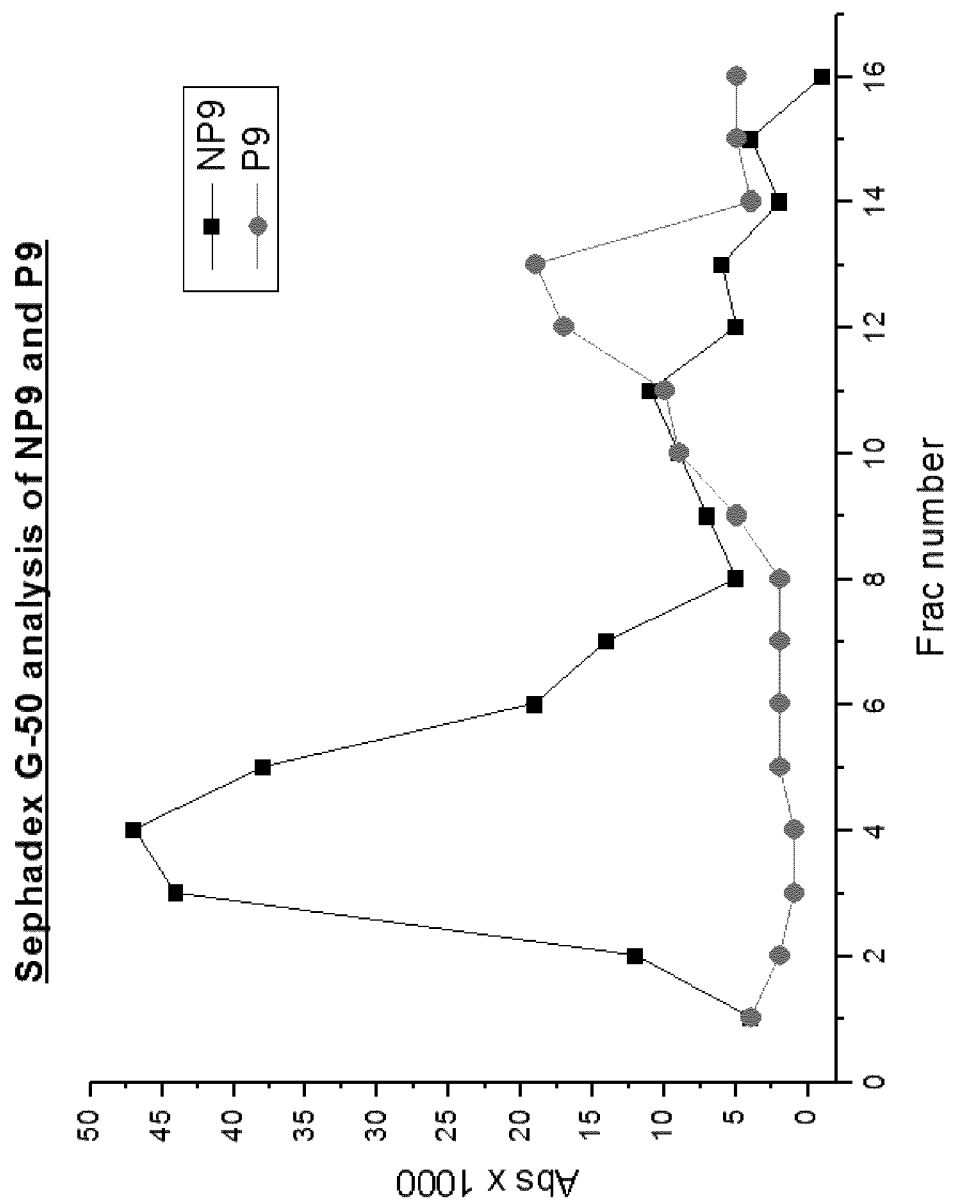
FIG. 2: GNP presentation compared to free peptide presentation: (A-B) GNPs 8 and 9 were separated by Sephadex column into 15 fractions, which were then analyzed by UV absorption for protein levels. The red line (indicated by circles) in FIG. 2A represents free peptide alone. (C-H) LKb cells were pulsed for 2 hrs with noted GNPs or corresponding free peptide at the noted concentration (1 ug/mL peptide (Green), 0.1 ug/mL (Blue), or 0.01 ug/mL (Red)). Readouts are by (C-F) flow cytometry or (G-H) B3Z assay. (I-N) LKb were pulsed with the noted free peptide for 2 hrs on ice (1-K) or at 37° C. (L-N). Next, cells were analyzed by flow cytometry for presentation of SIINFEKL (SEQ ID NO: 2). Red portions of the histogram represent positive staining as compared to unpulsed cells.
Figure 2B:
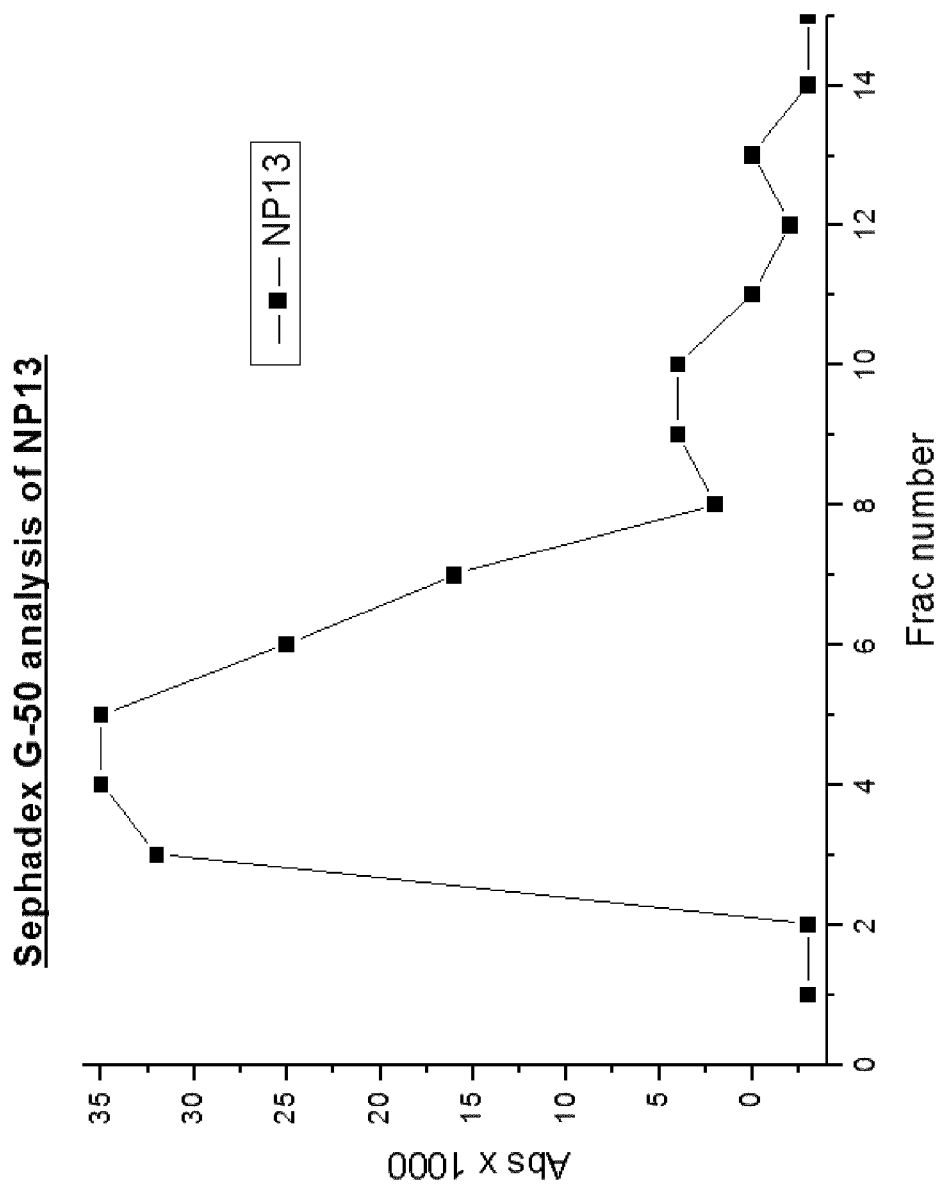
Figure 2C:
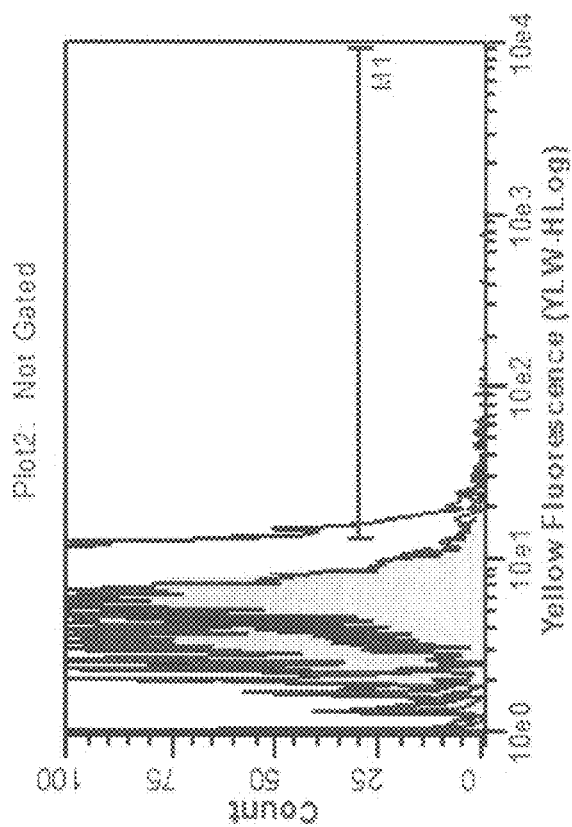
Figure 2C:
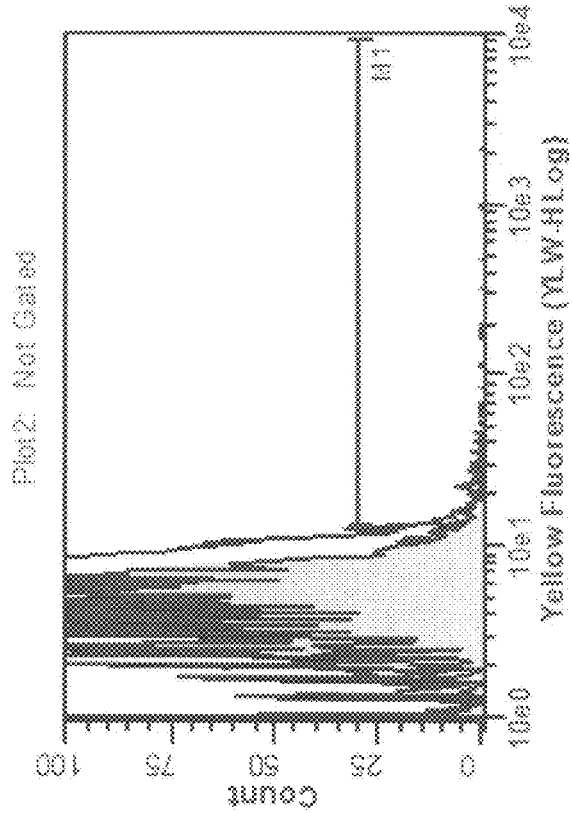
Figure 2D:
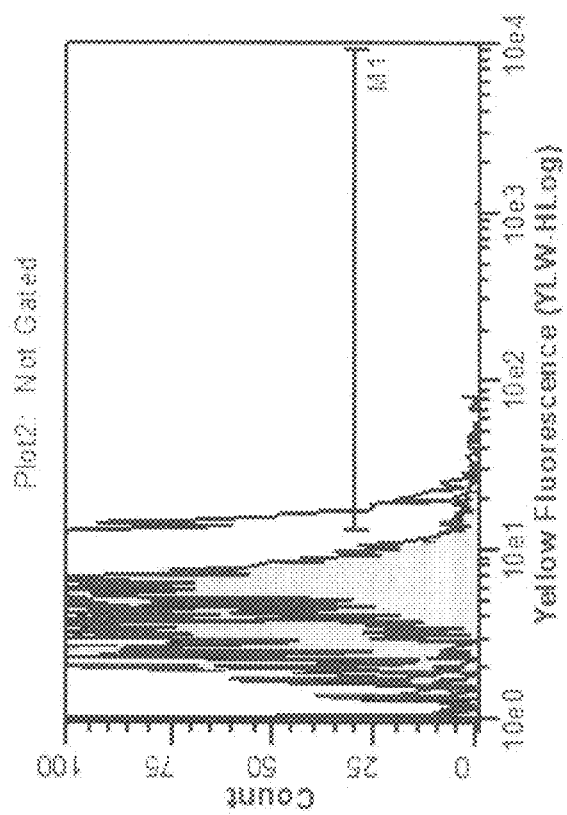
Figure 2D:
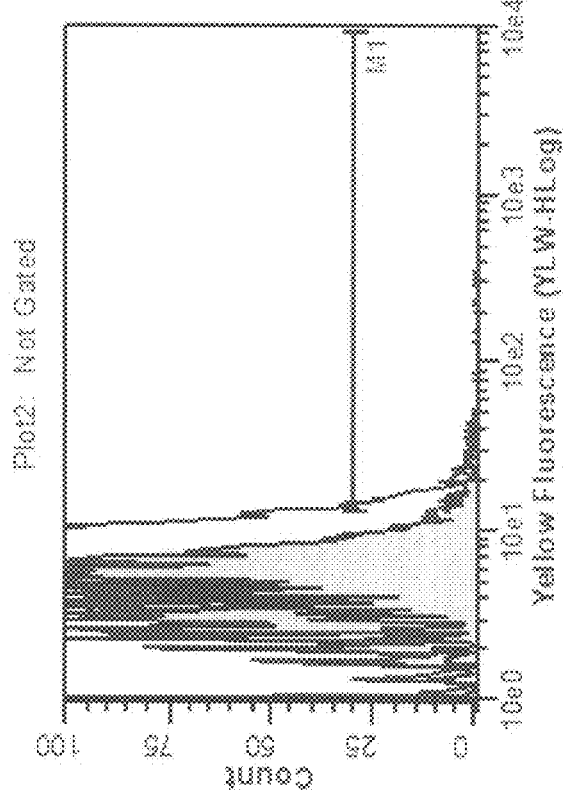
Figure 2E:
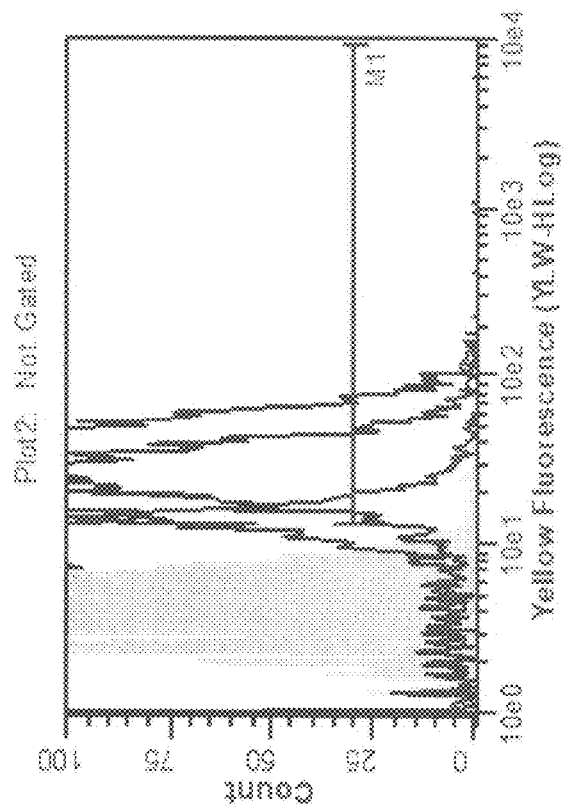
Figure 2E:
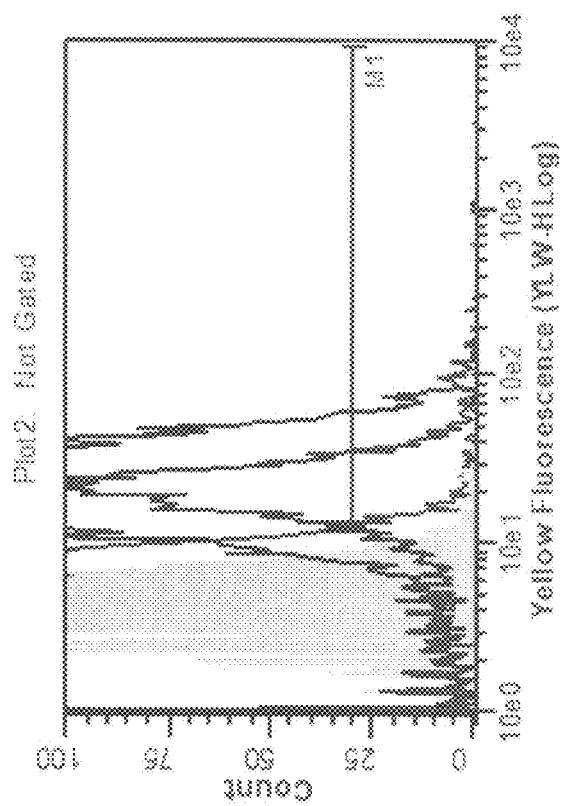
Figure 2F:
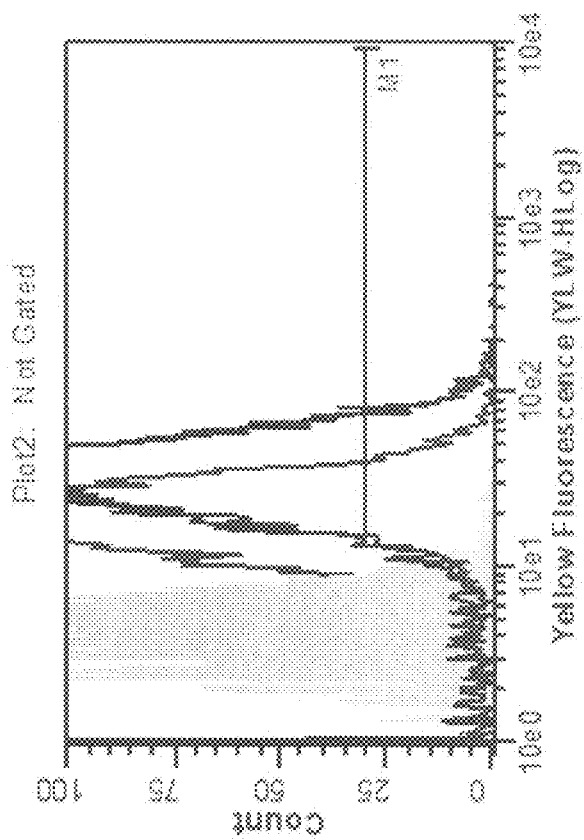
Figure 2F:
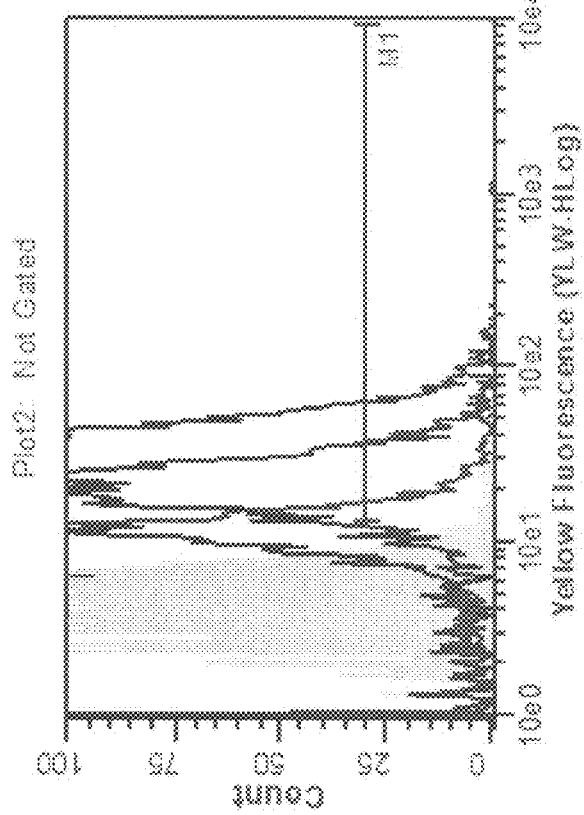
Figure 2G:
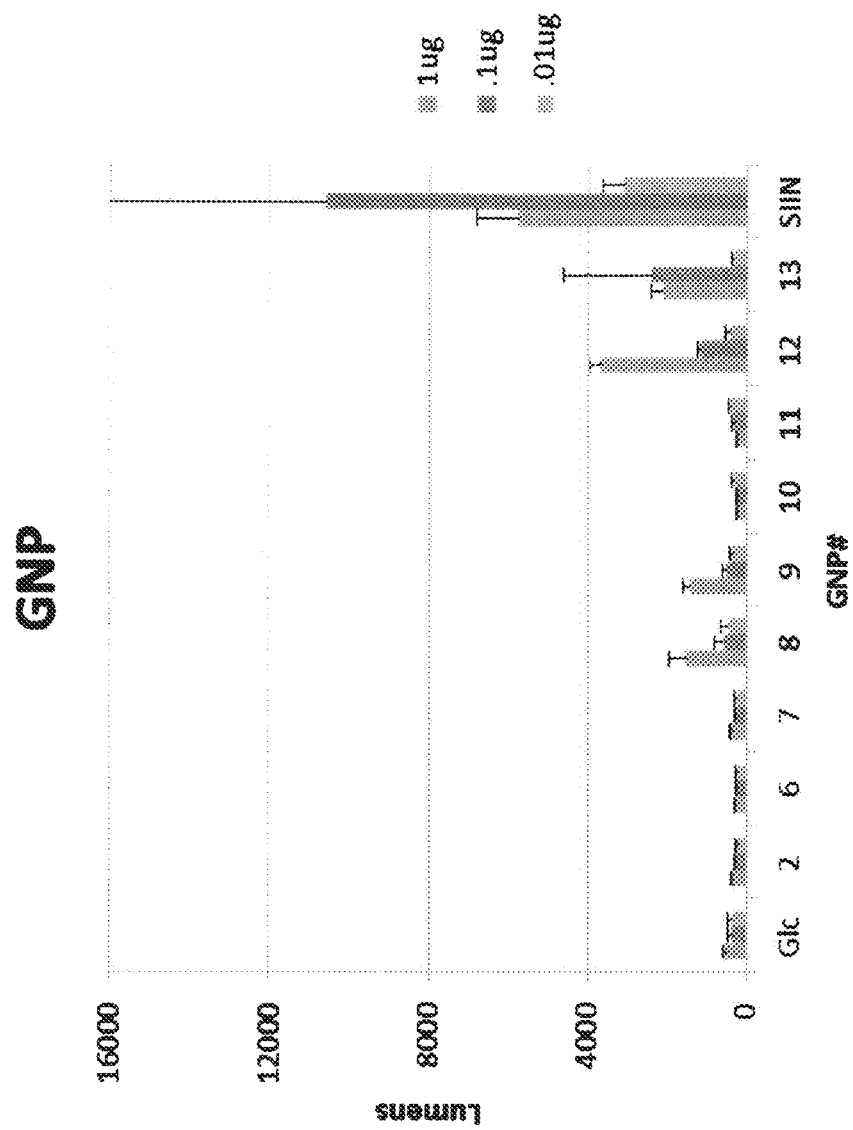
Figure 2I:
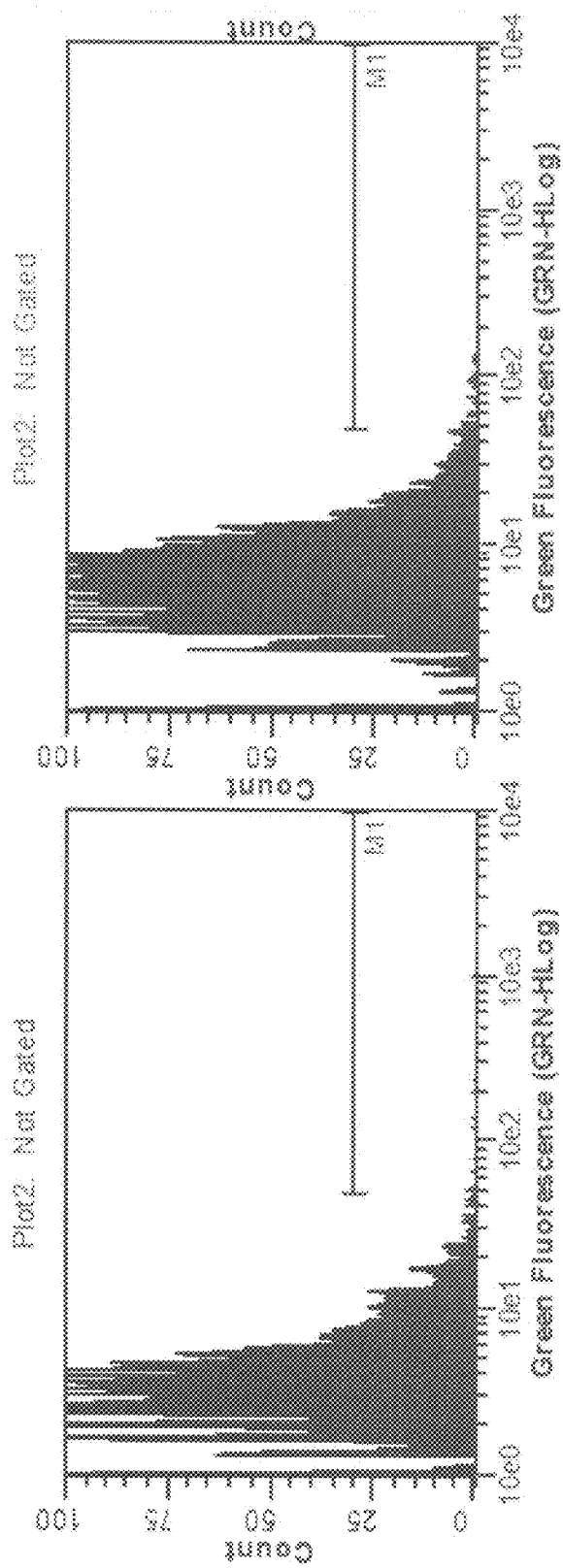
Figure 2J:
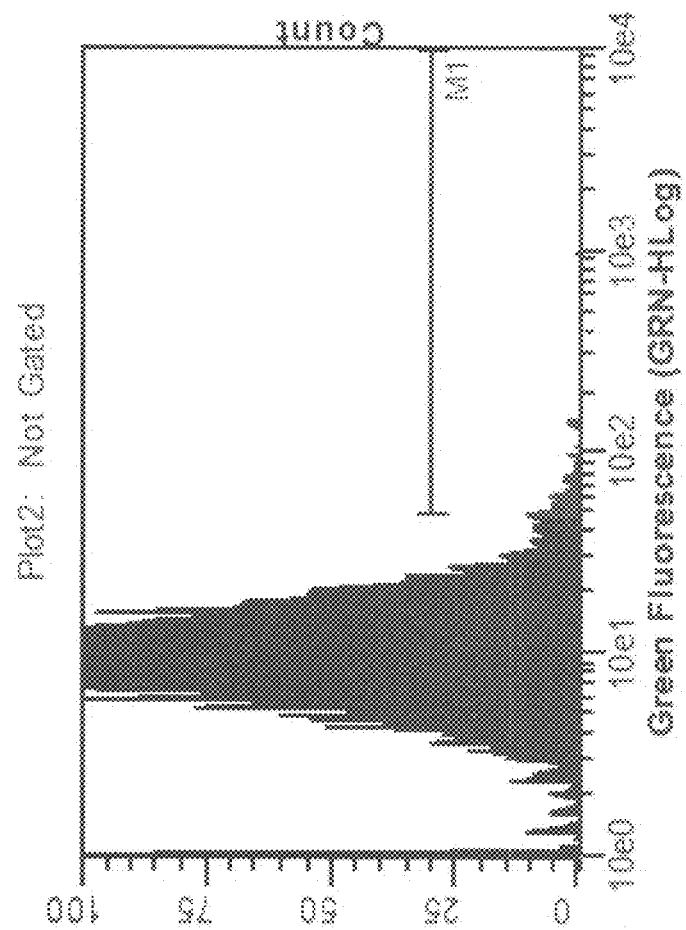
Figure 2K:
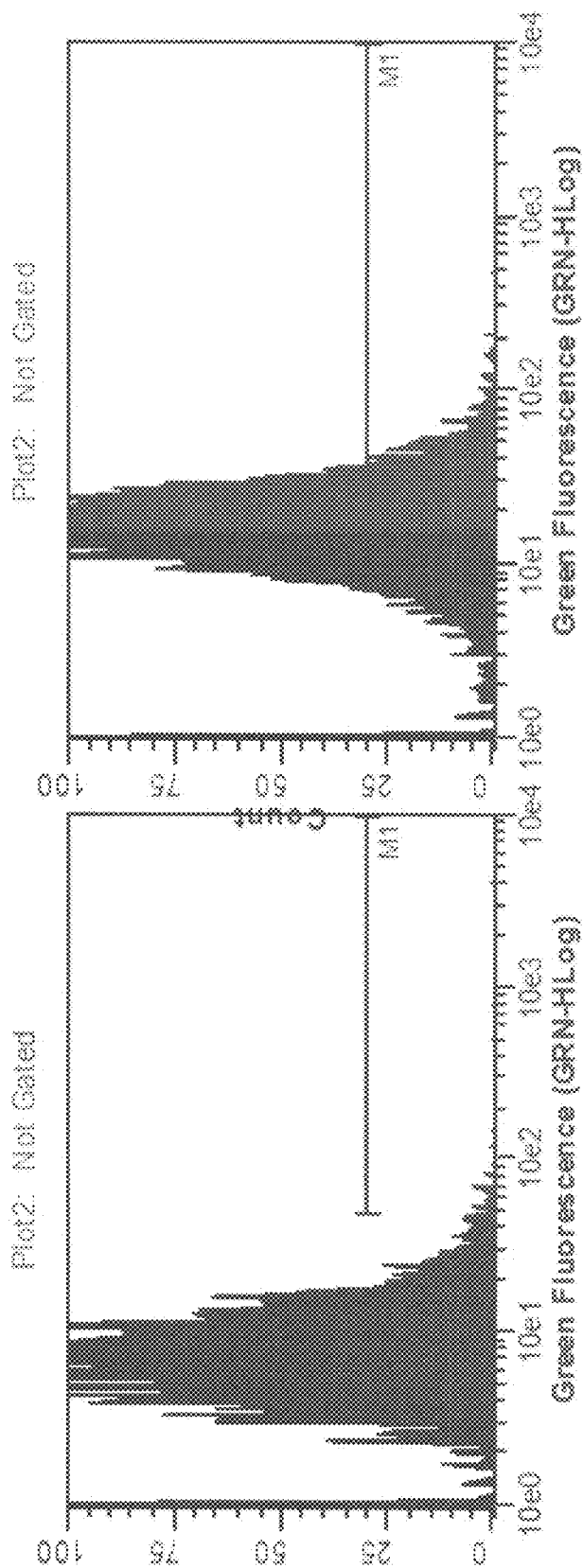
Figure 2L:
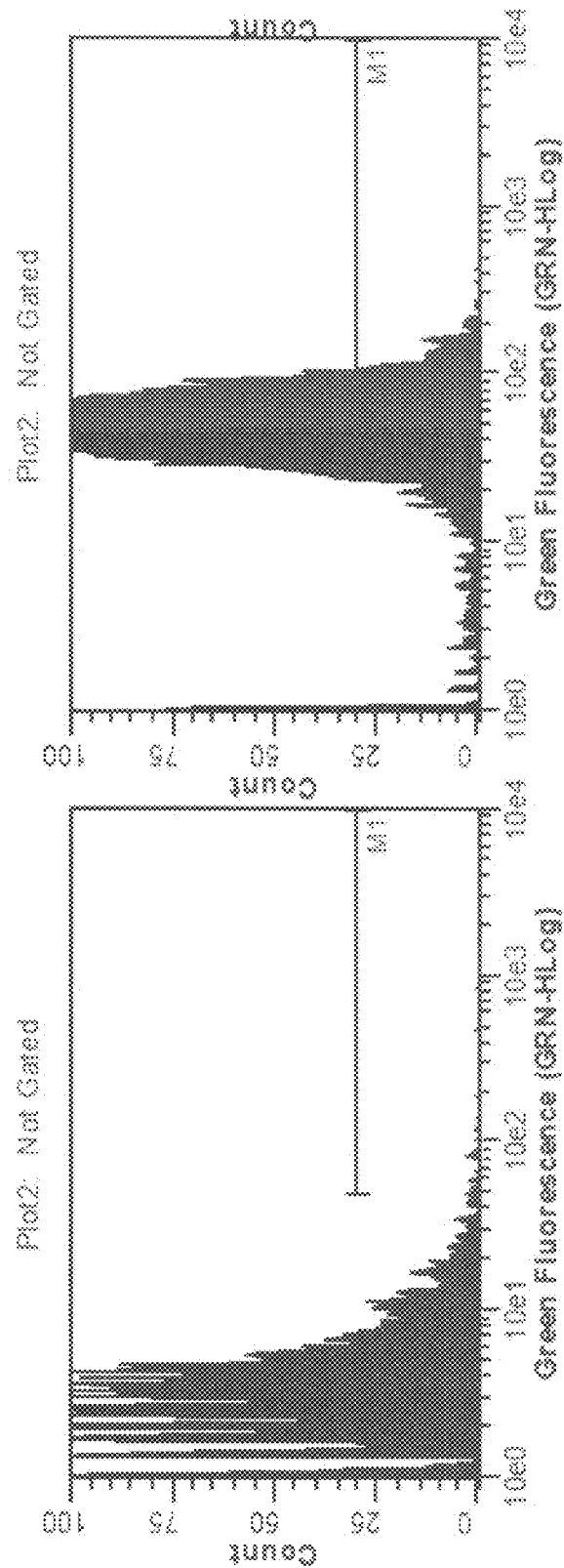
Figure 2M:
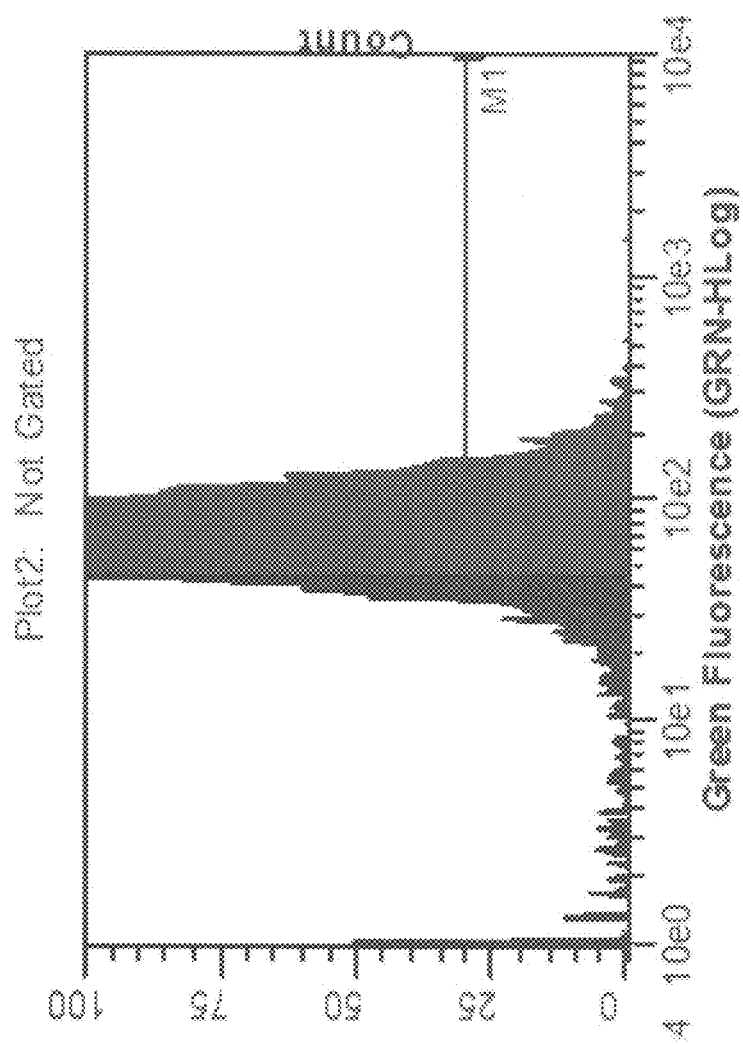
Figure 2N:
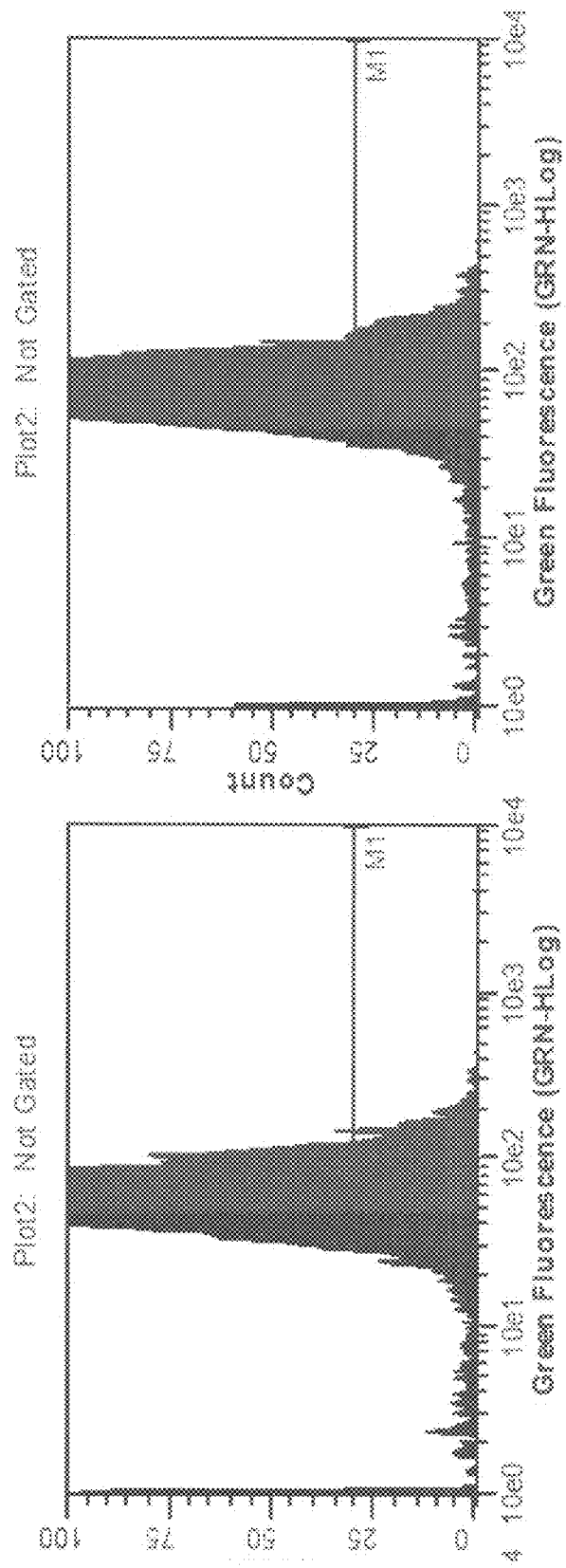

It was important to consider the possible effects of any free peptide present in the nanoparticle samples (FIGS. 2A-B). Therefore, we evaluated how efficiently corresponding free peptide from each preparation is presented. Similar to previous experiments, LKb cells were pulsed for 2 hrs with three concentrations of GNP or free peptide. Presentation was assessed by flow cytometry (FIGS. 2C-F) or B3Z assay (FIGS. 2G-H). From these results, we deduced that free peptide is presented well. Lastly, we sought to test whether processing is necessary for presentation of these free peptides. A test requires the pulsing of peptides on ice compared to 37° C. At 37° C., cells can take up peptide and process it within the endosome, however, on ice, peptide can only be loaded on the surface without processing. Indeed, we observed that free peptides with linkers generally need processing while the peptide without the linker can be presented (FIGS. 2I-N) without any processing.

C. Analysis of Preparations Lacking Free Peptide

Figure 3A:
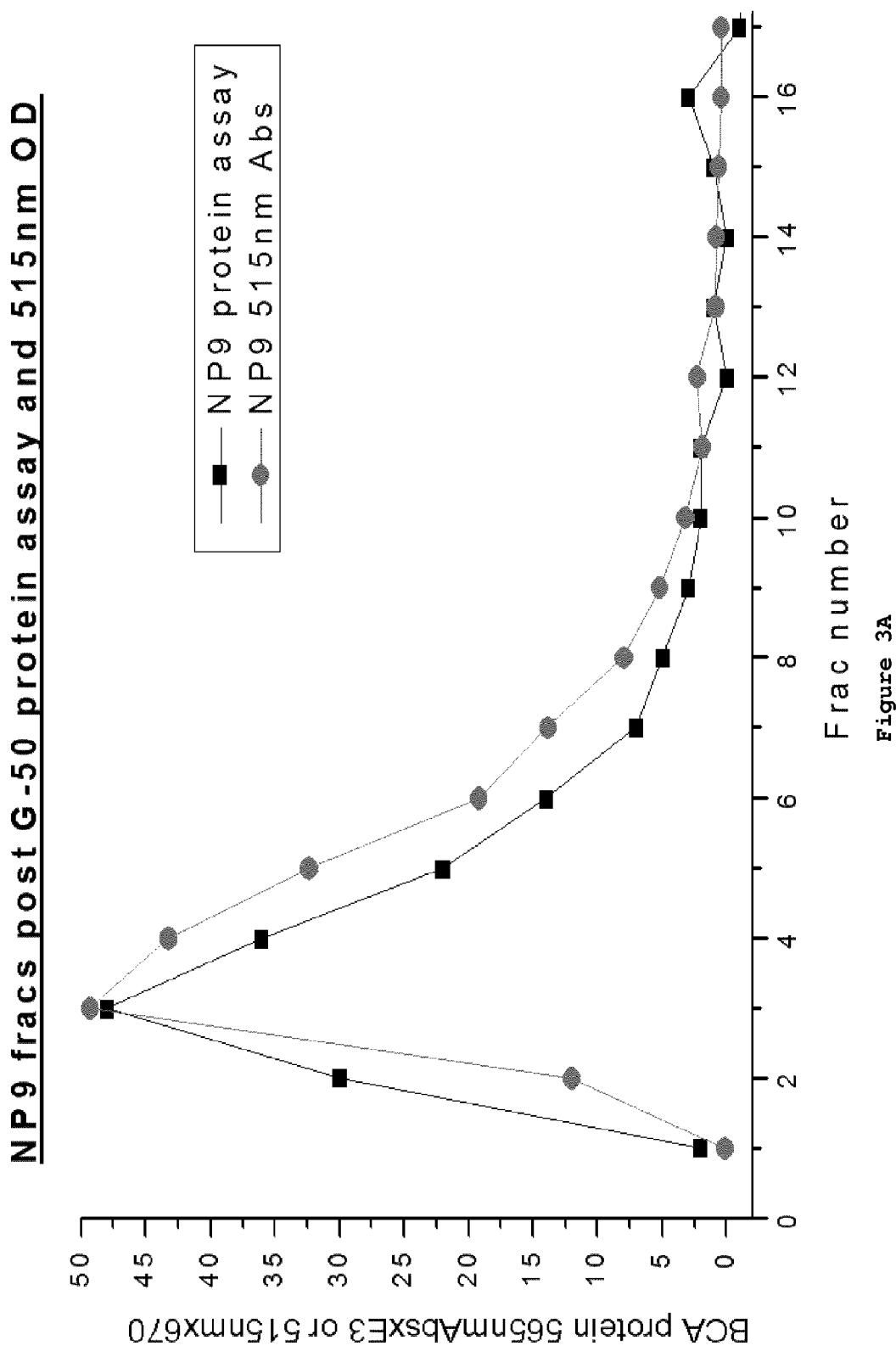
FIG. 3: GNP presentation from preparations lacking free peptide: (A-B) New preparations of GNPs 8 and 9 were separated by Sephadex G-50 column into 15 fractions, which were then analyzed by UV absorption for protein levels. Arrows indicate which fractions were pooled for further use. (C-E,F) LKb cells were pulsed for 2 hrs with noted previous preparations of GNPs (old GNP) or newer preparations from (A and B) (new GNP) at the noted concentrations (1 ug/mL peptide (Green), or 0.1 ug/mL (Red)). Readouts are by (C-E) flow cytometry or (F) B3Z assay.
Figure 3B:
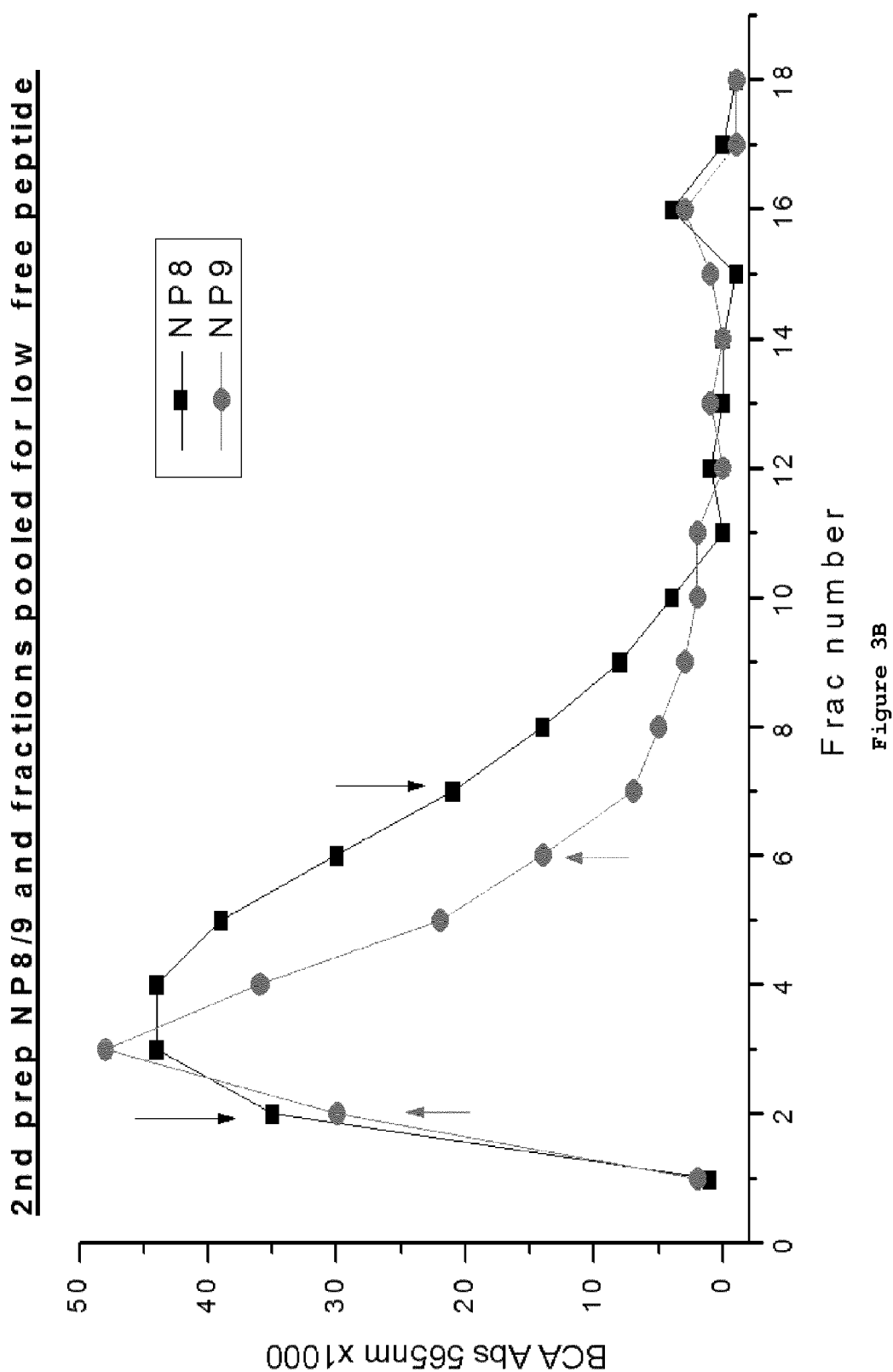
Figure 3C:
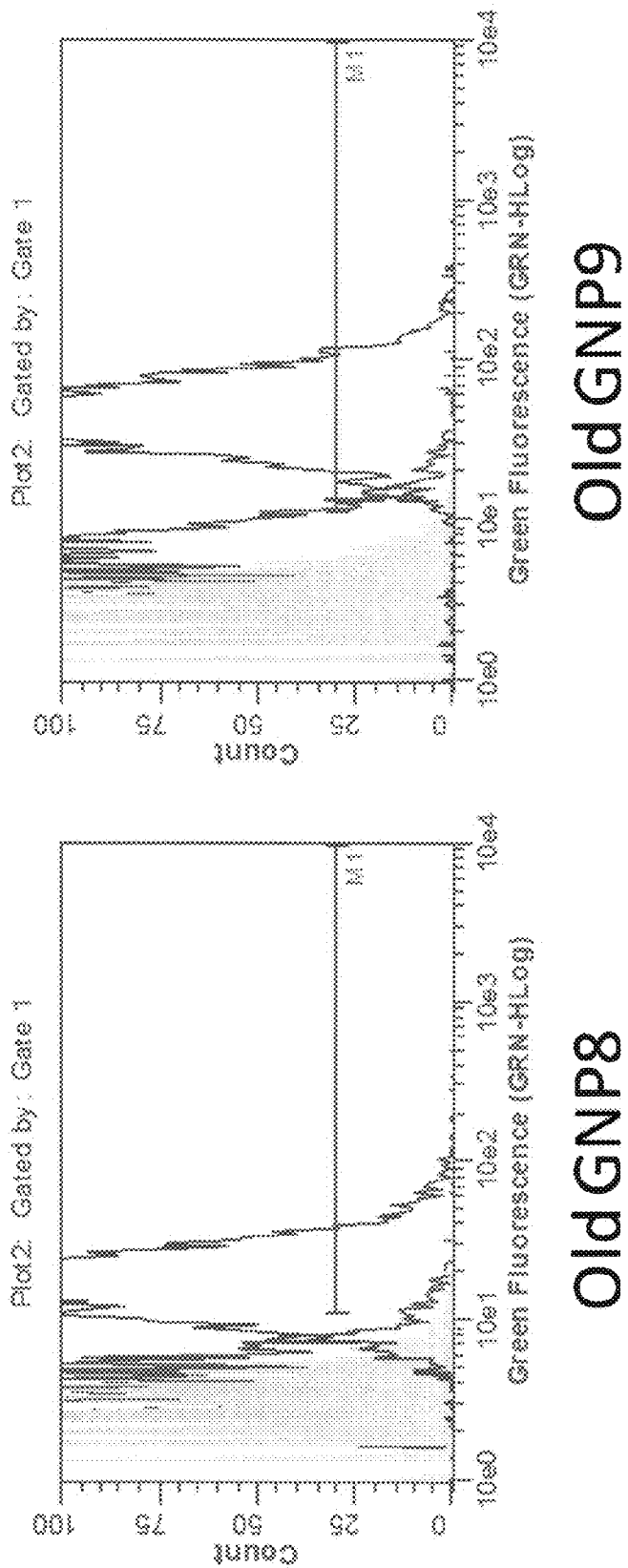
Figure 3D:
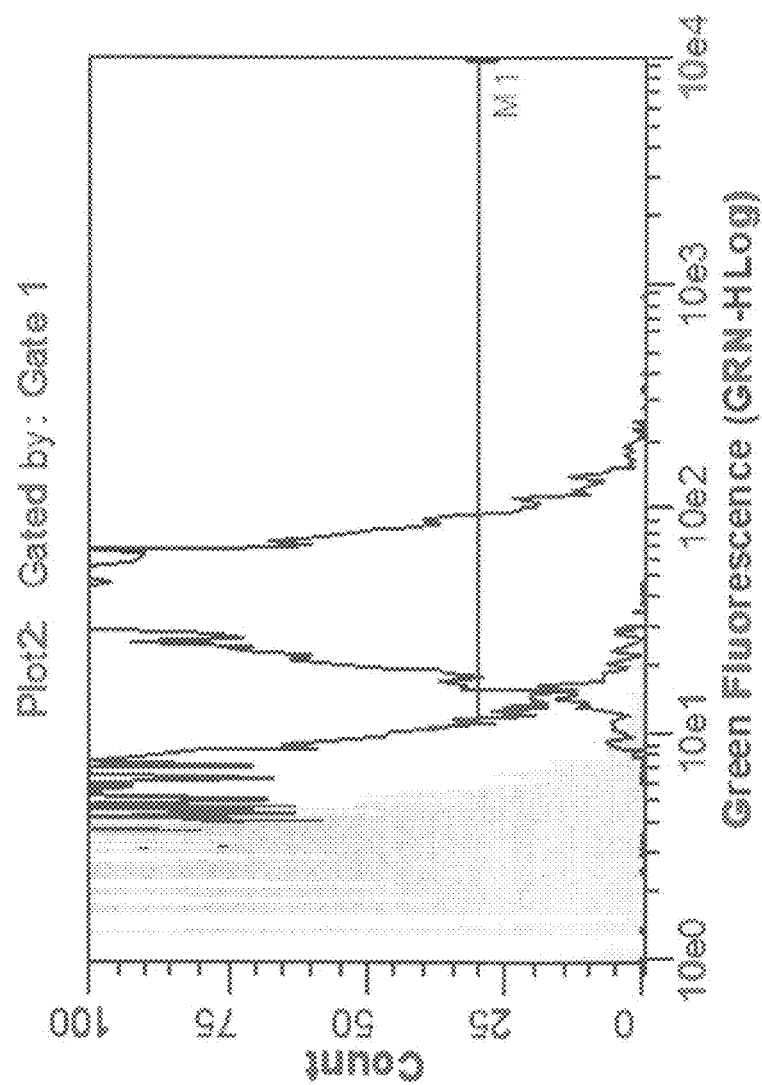
Figure 3E:
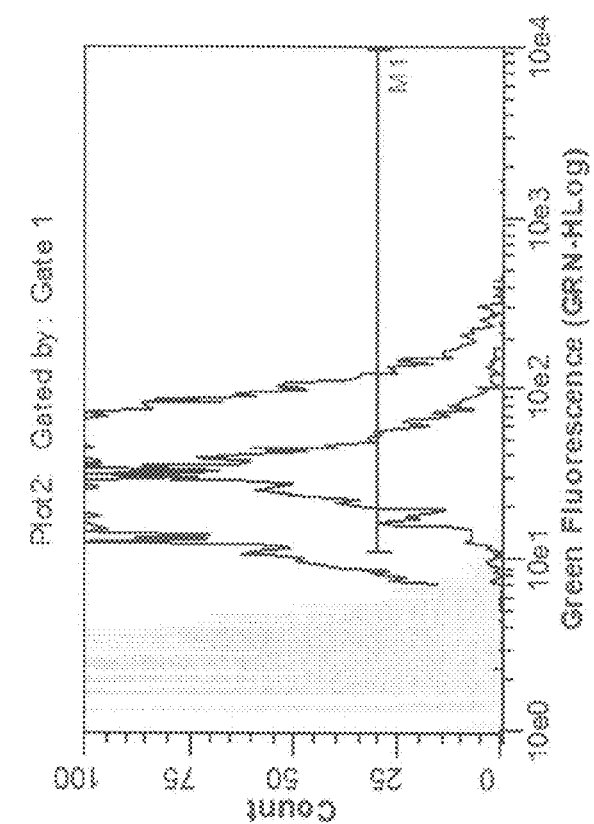
Figure 3E:
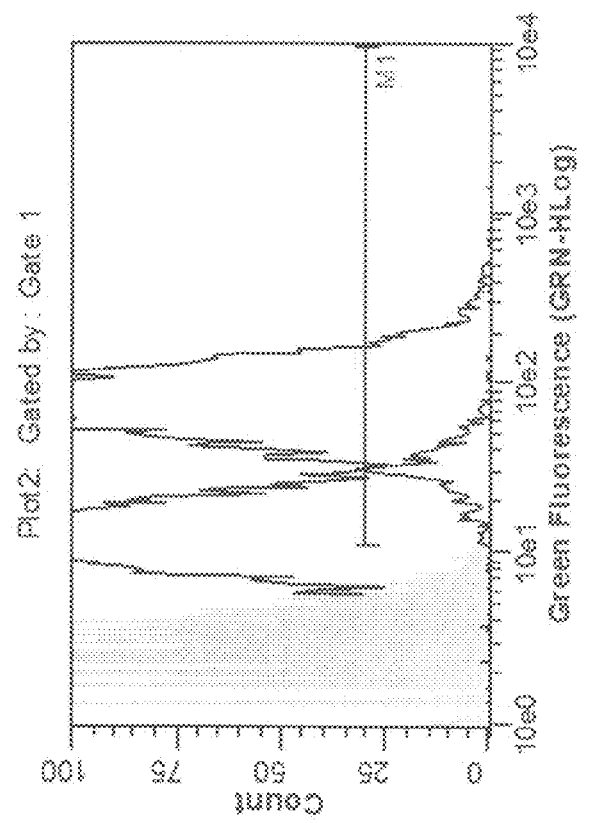

In view of the results demonstrating the possible effect of contaminating free peptides, purified preparations were made. Purification was carried out on the GNPs (8 and 9) using a Sephadex G-50 column removing all free peptide (FIGS. 3A-B). Lastly, above experiments were repeated using previous and newer preparations in the same assay. We extended the two-hour incubation to an overnight period, which has been shown to be sufficient for SIINFEKL (SEQ ID NO: 2) presentation (data not shown). Upon flow cytometric analysis, we observed that the samples lacking free peptide work just as well as those containing peptide (FIGS. 3C-E). These results were next confirmed using a B3Z assay (FIG. 3F). Therefore, it is clear that GNPs 8 and 9 serve as a viable option for peptide delivery to an antigen presenting cell for presentation of MHCI.

D. Conclusions

GNPs 8, 9, 12, and 13 are processed and presented very well compared to the others.

This corresponds to the sequences FLAAYSIINFEKL (SEQ ID NO: 4) and AAYSIINFEKL (SEQ ID NO: 5) being the best for in vitro SIINFEKL (SEQ ID NO: 2) presentation (peptide portion of the linker shown underlined).

HS—(CH2)10-(CH2OCH2)7-CONH chemistry is better processed than HS(CH2)2-CONH. However, HS(CH2)2-CONH is also processed very well while being more cost effective.

Contaminating free peptide may give rise to presentation.

Newer preparations, which lack free peptide, are also processed and presented well.

This suggests that GNPs 8 and 9 are efficiently processed for presentation of SIINFEKL (SEQ ID NO: 2).

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A nanoparticle comprising:
   (i) a core comprising a metal and/or a semiconductor atom;
   (ii) a corona comprising a plurality of ligands covalently linked to the core, wherein at least a first ligand of said plurality comprises a carbohydrate moiety that is covalently linked to the core via a first linker or comprises glutathione, and wherein at least a second ligand of said plurality comprises a peptide of choice that is covalently linked to the core via a second linker, said second linker comprising:
      a peptide portion and a non-peptide portion, wherein said peptide portion of said second linker comprises the sequence FLAAY (SEQ ID NO: 1).

2. The nanoparticle of claim 1, wherein said peptide of choice consists of a sequence of 8 to 12 amino acid residues and is an epitopic peptide that binds to a class I Major Histocompatibility Complex (MHC) molecule.

3. The nanoparticle according to claim 1, wherein said non-peptide portion of the second linker comprises C2-C15 alkyl and/or C2-C15 glycol.

4. The nanoparticle according to claim 1, wherein said first ligand and/or said second ligand are covalently linked to the core via a sulphur-containing group, an amino-containing group, a phosphate-containing group or an oxygen-containing group.

5. The nanoparticle according to claim 1, wherein the peptide of choice is an epitopic peptide that is presented by a class I MHC molecule so as to stimulate a Cytotoxic T Lymphocyte (CTL) response.

6. The nanoparticle according to claim 1, wherein the peptide of choice forms at least a portion of or is derived from a Tumour-Associated Antigen (TAA) or a viral-, bacterial-, or parasite-associated antigen.

7. The nanoparticle according to claim 6, wherein the TAA is a lung cancer antigen.

8. The nanoparticle according to claim 1 wherein:
   (i) the carbohydrate moiety of said first ligand comprises a monosaccharide and/or a disaccharide; and/or
   (ii) said plurality of ligands comprises at least one glutathione ligand covalently linked to the core of the nanoparticle via the glutathione sulphur atom; and/or
   (iii) said plurality of ligands comprises:
      (a) glucose;
      (b) N-acetylglucosamine;
      (c) glutathione;
      (d) glucose and N-acetylglucosamine;
      (e) glucose and glutathione;
      (f) N-acetylglucosamine and glutathionie; or
      (g) glucose, N-acetylglucosamine and glutathione.

9. The nanoparticle according to claim 1, wherein said first linker comprises C2-C15 alkyl and/or C2-C15 glycol.

10. The nanoparticle according to claim 1, wherein said first ligand comprises 2'-thioethyl-β-D-glucopyranoside or 2'-thioethyl-α-D-glucopyranoside covalently attached to the core via the thiol sulphur atom.

11. The nanoparticle according to claim 1, wherein the plurality of ligands are in a molar ratio of carbohydrate-containing ligands and/or glutathione ligands to peptide of choice containing ligands in the range of 5:1 to 100:1.

12. The nanoparticle according to claim 1, wherein the diameter of the core of the nanoparticle is in the range 1 nm to 5 nm.

13. The nanoparticle according to claim 1, wherein the core comprises a metal selected from the group consisting of: Au, Ag, Cu, Pt, Pd, Fe, Co, Gd, Zn and any combination of said metals.

14. A composition comprising a plurality of nanoparticles as defined in claim 1, and at least one pharmaceutically acceptable carrier, salt and/or diluents.

15. The composition according to claim 14, wherein the composition comprises a first species of nanoparticle having a first peptide of choice-containing ligand and a second species of nanoparticle having a second peptide of choice-containing ligand, wherein the peptides of choice of said first and second species differ.

16. The composition according to claim 14, further comprising at least one adjuvant covalently attached to the core of at least one nanoparticle.

17. The composition according to claim 16, wherein the adjuvant comprises (S)-(2,3-bis(palmitoyloxy)-(2RS)-propyl)-N-palmitoyl-(R)-Cys-(S)-Ser(S)-Lys$_4$-OH (Pam$_3$Cys).

18. A vaccine comprising a composition as defined in claim 14.

* * * * *

```
                         SEQUENCE LISTING

<160> NUMBER OF SEQ ID NOS: 6

<210> SEQ ID NO 1
<211> LENGTH: 5
<212> TYPE: PRT
<213> ORGANISM: Artificial sequence
<220> FEATURE:
<223> OTHER INFORMATION: Synthetic sequence: Linker

<400> SEQUENCE: 1

Phe Leu Ala Ala Tyr
1               5

<210> SEQ ID NO 2
<211> LENGTH: 8
<212> TYPE: PRT
<213> ORGANISM: Gallus gallus

<400> SEQUENCE: 2

Ser Ile Ile Asn Phe Glu Lys Leu
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic sequence: Test ligand

<400> SEQUENCE: 3

Phe Leu Ser Ile Ile Asn Phe Glu Lys Leu
1               5                   10

<210> SEQ ID NO 4
<211> LENGTH: 13
<212> TYPE: PRT
<213> ORGANISM: Artificial sequence
<220> FEATURE:
<223> OTHER INFORMATION: Synthetic sequence: Test ligand

<400> SEQUENCE: 4

Phe Leu Ala Ala Tyr Ser Ile Ile Asn Phe Glu Lys Leu
1               5                   10

<210> SEQ ID NO 5
<211> LENGTH: 11
<212> TYPE: PRT
<213> ORGANISM: Artificial sequence
<220> FEATURE:
<223> OTHER INFORMATION: Synthetic sequence: Test ligand

<400> SEQUENCE: 5

Ala Ala Tyr Ser Ile Ile Asn Phe Glu Lys Leu
1               5                   10

<210> SEQ ID NO 6
<211> LENGTH: 4
<212> TYPE: PRT
<213> ORGANISM: Gallus gallus

<400> SEQUENCE: 6

Ser Ile Ile Asn
1
```